(12) United States Patent
Bleske et al.

(10) Patent No.: US 11,433,063 B1
(45) Date of Patent: Sep. 6, 2022

(54) INTRANASAL COMPOSITION OF PHARMACEUTICAL COUNTERMEASURES FOR CHEMICAL WARFARE NERVE AGENTS AND ACCIDENTAL EXPOSURE TO ORGANOPHOSPHATE PESTICIDES

(71) Applicant: Belhaven BioPharma Inc., Durham, NC (US)

(72) Inventors: Barry Bleske, Albuquerque, NM (US); Ted William Lanpher, Half Moon Bay, CA (US)

(73) Assignee: BELHAVEN BIOPHARMA, INC., Durham, NC (US)

( * ) Notice: Subject to any disclaimer, the term of this patent is extended or adjusted under 35 U.S.C. 154(b) by 0 days.

(21) Appl. No.: 17/687,167

(22) Filed: Mar. 4, 2022

Related U.S. Application Data

(63) Continuation-in-part of application No. 17/349,507, filed on Jun. 16, 2021, which is a continuation of application No. 16/814,997, filed on Mar. 11, 2020, now abandoned.

(60) Provisional application No. 62/919,392, filed on Mar. 12, 2019.

(51) Int. Cl.

| | |
|---|---|
| *A61K 31/46* | (2006.01) |
| *A61K 31/5513* | (2006.01) |
| *A61M 15/08* | (2006.01) |
| *A61K 31/137* | (2006.01) |
| *A61K 9/00* | (2006.01) |
| *A61K 31/4425* | (2006.01) |

(52) U.S. Cl.
CPC ............ *A61K 31/46* (2013.01); *A61K 9/0043* (2013.01); *A61K 9/0075* (2013.01); *A61K 31/137* (2013.01); *A61K 31/4425* (2013.01); *A61K 31/5513* (2013.01); *A61M 15/08* (2013.01); *A61M 2202/064* (2013.01)

(58) Field of Classification Search
CPC .... A61K 31/46; A61K 9/0043; A61K 9/0075; A61K 31/137; A61K 31/4425; A61K 31/5513; A61M 15/08; A61M 2202/064
See application file for complete search history.

(56) References Cited

U.S. PATENT DOCUMENTS

| | | | |
|---|---|---|---|
| 7,947,742 | B2 | 5/2011 | Batycky et al. |
| 7,954,491 | B2 | 6/2011 | Hrkach |
| 8,337,817 | B2 | 12/2012 | Nagata et al. |
| 8,415,397 | B2 | 4/2013 | Batycky et al. |
| 8,747,813 | B2 | 6/2014 | Batycky et al. |
| 9,789,071 | B2 | 10/2017 | Fleming |
| 10,765,602 | B1 | 9/2020 | Arnett et al. |
| 2012/0111324 | A1 | 5/2012 | Kraft et al. |
| 2014/0014104 | A1 | 1/2014 | Hoekman et al. |
| 2015/0094378 | A1 | 4/2015 | Batycky et al. |
| 2015/0231130 | A1* | 8/2015 | Wynne ................. A61M 11/007 514/282 |
| 2015/0366950 | A1 | 12/2015 | Rosenberg |
| 2016/0220489 | A1 | 8/2016 | Fleming et al. |
| 2017/0119699 | A1 | 5/2017 | Batycky et al. |
| 2017/0136035 | A1 | 5/2017 | Cafiero et al. |
| 2021/0361770 | A1 | 11/2021 | Lowenthal et al. |
| 2021/0401825 | A1 | 12/2021 | Sävmarker et al. |

OTHER PUBLICATIONS

Website: Amazon.com _ 2 Pack Molle Pouches—Tactical Compact Water-Resistant EDC Pouch (CP) _ Sports & Outdoors, available Mar. 5, 2019. (Year: 2019).*

Armenian P, Campagne D, Stroh G, Ives Tailman C, Zeng WZD, Lin T, Gerona RR. Hot and Cold Drugs: National Park Service Medication Stability at the Extremes of Temperature. Prehosp Emerg Care. May-Jun. 2017;2(3):378-385. doi: 10.1080/10903127. 2016.1258098. Epub Jan. 6, 2017. PMID: 28059581.

Bailey AM, Baker SN, Baum RA, Chandler HE, Weant KA. Being prepared: emergency treatment following a nerve agent release. Adv Emerg Nurs J. Jan.-Mar. 2014;36(1):22-33; quiz 34-5. doi: 10.1097/ TME.0000000000000008. PMID: 24487260.

Barry E Bleske, Eric W Warren, Ted L Rice, Michael J Shea, Gordon Amidon, Paul Knight, Comparison of intravenous and intranasal administration of epinephrine during CPR in a canine model, Annals of Emergency Medicine, vol. 21, Issue 9, 1992, pp. 1125-1130, ISSN 0196-0644, https://doi.org/10.1016/S0196-0644(05)80657-2.

Barry E Bleske, Ted L Rice, Eric W Warren, Donald A Giacherio, Lori J Gilligan, Kenneth D Massey, Alan R Tait, Effect of dose on the nasal absorption of epinephrine during cardiopulmonary resuscitation, The American Journal of Emergency Medicine, vol. 14, Issue 2, 1996, pp. 133-138, ISSN 0735-6757, https://doi.org/10.1016/S0735-6757(96)90119-9.

Bleske, B.E., Rice, T.L., Warren, E.W., Giacherio, D.A., Gilligan, L.J., Massey, K.D., Chrisp, C.E. and Tait, A.R. (1996), Effect of Vehicle on the Nasal Absorption of Epinephrine During Cardiopulmonary Resuscitation. Pharmacotherapy: The Journal of Human Pharmacology and Drug Therapy, 16: 1039-1045. https://doi.org/10.1002/j.1875-9114.1996.tb03030.x.

COMTAN® Prescribing Information 1999 (Year: 1999).

(Continued)

*Primary Examiner* — James D. Anderson
*Assistant Examiner* — William Y Lee
(74) *Attorney, Agent, or Firm* — NEO IP

(57) ABSTRACT

Nasally targeted dry powder compositions and methods for their use in the treatment of exposure to organophosphate compounds including chemical warfare agents and pesticides. Compositions include anticholinergic agents and cholinesterase reactivator agents used for primary treatment and vasoactive agents and benzodiazepines used for secondary treatment of exposure, and combinations of these agents. Compositions incorporate excipients and enabling agents such as permeation enhancers, and optimal sizing of active pharmaceutical ingredient particle size to improve drug delivery across the nasal mucosa, stability, and resistance to heat degradation. Packaging and configuration of devices for dry powder nasal compositions enable their use by non-medical personnel in civilian mass casualty or battlefield environments.

20 Claims, 6 Drawing Sheets

(56) References Cited

OTHER PUBLICATIONS

Crowe TP, Greenlee MHW, Kanthasamy AG, Hsu WH. Mechanism of intranasal drug delivery directly to the brain. Life Sci. Feb. 15, 2018;195:44-52. doi: 10.1016/j.lfs.2017.12.025. Epub Dec. 22, 2017. PMID: 29277310.

Management Guidelines for Nerve Agents: Tabun (GA); Sarin (GB); Soman (GD); and VX, by Agency for Toxic Substances and Disease Registry, 2011 Retrieved from http://www.atsdr.cdc.gov/MHMI/mmg166.pdf.

Manthripragada et al. Epidemiology. Jan. 2010; 21 (1): 87-94. (Year: 2010).

Pashirova TN, Zueva IV, Petrov KA, Lukashenko SS, Nizameev IR, Kulik NV, Voloshina AD, Almasy L, Kadirov MK, Masson P, Souto EB, Zakharova LY, Sinyashin OG. Mixed cationic liposomes for brain delivery of drugs by the intranasal route: The acetylcholinesterase reactivator 2-PAM as encapsulated drug model. Colloids Surf B Biointerfaces. Nov. 1, 2018;171:358-367. doi: 10.1016/j.colsurfb.2018.07.049. Epub Jul. 24, 2018. PMID: 30059851.

Pharmacokinetics of Epinephrine Absorption via Intranasal Administration: A Preliminary Report, Abstract Only, vol. 125, ISSUE 2, SUPPLEMENT 1, 859, AB219, Feb. 1, 2010, DOI:https://doi.org/10.1016/j.jaci.2009.12.857.

Sravanthi Gundavarapu, Jianguo Zhuang, Edward G. Barrett, Fadi Xu, . . . Mohan L. Sopori, A critical role of acute bronchoconstriction in the mortality associated with high-dose sarin inhalation: Effects of epinephrine and oxygen therapies, vol. 274, Issue 2, pp. 200-208, Jan. 15, 2014.

Thiermann H, Steinritz D, Worek F, Radtke M, Eyer P, Eyer F, Felgenhauer N, Zilker T. Atropine maintenance dosage in patients with severe organophosphate pesticide poisoning. Toxicol Lett. Sep. 25, 2011;206(1):77-83. doi: 10.1016/j.toxlet.2011.07.006. Epub Jul. 8, 2011. PMID: 21771644.

Verma, R., & Garg, S. (2001). Current Status of Drug Delivery Technologies and Future Directions.

\* cited by examiner

INTRANASAL COMPOSITION OF PHARMACEUTICAL COUNTERMEASURES FOR CHEMICAL WARFARE NERVE AGENTS AND ACCIDENTAL EXPOSURE TO ORGANOPHOSPHATE PESTICIDES

CROSS REFERENCES TO RELATED APPLICATIONS

This application is related to and claims priority from the following U.S. patents and patent applications. This application is a continuation-in-part of U.S. patent application Ser. No. 17/349,507, filed Jun. 16, 2021, which is a continuation of U.S. patent application Ser. No. 16/814,997, filed Mar. 11, 2020, which claims priority to U.S. Provisional Patent Application No. 62/919,392, filed Mar. 12, 2019, each of which is incorporated herein by reference in its entirety.

BACKGROUND OF THE INVENTION

1. Field of the Invention

The present invention relates to medical counter measures, and more specifically to dry powder compositions and methods of treatment of organophosphate exposure using the dry power compositions.

2. Description of the Prior Art

It is generally known in the prior art to provide medications for the treatment of various conditions. Medications are often delivered intravenously and by needle and syringe injection, which may be subcutaneous or intra-muscular. Increasingly, medications are delivered by auto-injectors, which may be used within medical facilities or in ambulatory settings by medical and non-medical personnel, caregivers, and patients themselves. Self-administration via auto-injector has dramatically improved the availability of treatment with medications in emergency situations. Alternatives that do not require a needle or syringe have been explored in the prior art.

Prior art patent documents include the following:

U.S. Patent Publication No. 20120111324 for Dry powder drug delivery compositions, methods of use, and devices therefore by inventors Kraft, et al., filed Oct. 22, 2008 and published May 10, 2012, is directed to systems, methods, and compositions for the pulmonary administration of one or more therapeutic agents, in dry powder form, in a single, large dose quantity. These compositions, methods, and systems are useful in the treatment of patients suffering from toxic or harmful gas exposure, such as nerve gas exposure, as well as in the treatment of patients suffering from diseases of the pulmonary system, including tuberculosis, cystic fibrosis, and chronic obstructive pulmonary disease (COPD).

U.S. Patent Publication No. 20140014104 for Nasal delivery device by inventors Hoekman, et al., filed Sep. 3, 2013 and published Jan. 24, 2017, is directed to a compound delivery device for delivering a plume derived from a propellant and a drug composition. The drug composition is in an intranasal dosage form in the form of powder, suspension, dispersion or liquid. The propelled intranasal dosage form is deposited within the olfactory region of the nasal cavity. The drug deposited within the olfactory region is delivered to the brain avoiding the blood-brain-barrier. Hydrofluoroalkane propellant from a pressurized canister is channeled to a diffuser and drug-containing chamber where the intra-nasal dosage form is aerosolized. The aerosolized intra-nasal dosage form passes through a nozzle thus delivering a plume to the olfactory region of a user's nasal cavity.

U.S. Pat. No. 10,765,602 for Medication delivery systems and methods by inventors Arnett, et al., filed Sep. 23, 2019 and issued Sep. 8, 2020, is directed to a medication delivery system including a medication administration device, a medication within the medication administration device, a container defining a cavity receiving the medication administration device, and a cap attached to the container and sealing the medication administration device within the cavity. The medication administration device includes an actuator extending from a body and operable to expel the medication by depressing the actuator into the body. The cap includes hold down members positioned to bear against the body of the medication administration device to prevent movement of the medication administration device toward the cap beyond a predetermined distance. The medication administration device is thereby prevented, inter alia, from prematurely discharging the medication during storage and transport.

U.S. Patent Publication No. 20210361770 for Intranasal epinephrine compositions and methods for the treatment of disease by inventors Lowenthal, et al., filed Aug. 6, 2021 and published Nov. 25, 2021, is directed to drug products adapted for nasal delivery comprising compositions with epinephrine and devices comprising such compositions. Methods of treating anaphylaxis with epinephrine products are also provided.

U.S. Patent Publication No. 20210401825 for Pharmaceutical composition for nasal delivery by inventors Sävmarker, et al., filed Feb. 10, 2021 and published Dec. 30, 2021, is directed to a solid pharmaceutical composition for nasal delivery of an opioid antagonist, comprising a pharmacologically-effective amount of an opioid antagonist and a pharmaceutically-acceptable carrier. Said compositions are preferably in the form of a powder produced by spray-drying, which are subsequently loaded into single use nasal applicators. Preferred pharmaceutically-acceptable carriers in this regard include disaccharides (e.g. lactose or trehalose) and dextrins (e.g. cyclodextrins or maltodextrins), preferably spray-dried together in combination. Compositions may further comprise an alkyl saccharide, preferably a sucrose ester, such as sucrose monolaurate. Said compositions and applicators may be employed in the treatment of opioid overdose in subjects.

SUMMARY OF THE INVENTION

The present invention relates to systems to counteract the medical complications associated with organophosphate exposure (e.g., due to chemical warfare, such as nerve agents) including clinical toxicity associated with acetylcholine excess which may include respiratory failure, bronchoconstriction, hypotensive shock, bradycardia, hypertension, seizures, cardiac arrest, or other situations requiring the need to implement cardiopulmonary resuscitation (CPR) and/or basic or advanced cardiac life support (ACLS). Disclosed herein are dry powder compositions and unit doses that include vasoactive and non-vasoactive agents (e.g., atropine, pralidoxime chloride, epinephrine, and/or diazepam) suitable for intranasal administration, methods of making the compositions, delivery devices and packaging to improve their effectiveness in emergency treatment settings, and methods of using the compositions to treat the effects of exposure to organophosphate agents.

It is an object of this invention to provide dry powder compositions and unit doses for treatment of organophosphate exposure.

In one embodiment, the present invention provides a device for intranasal administration of a pharmaceutical composition including a reservoir and a means for discharging one or more doses of the pharmaceutical composition, wherein the reservoir is operable to contain a quantity of the pharmaceutical composition, wherein the pharmaceutical composition includes an anti-muscarinic agent, wherein the anti-muscarinic agent is atropine or a pharmaceutically acceptable salt thereof, a cholinesterase reactivator, wherein the cholinesterase reactivator is 2-pyridine aldoxime methyl chloride, a vasoactive agent, wherein the vasoactive agent is epinephrine or a pharmaceutically acceptable salt thereof, and an anti-convulsant agent, wherein the anti-convulsant agent is diazepam or a pharmaceutically acceptable salt thereof.

In another embodiment, the present invention provides a kit for intranasal administration of a pharmaceutical composition including at least one device, wherein each of the at least one device includes a reservoir and a means for discharging one or more doses of the pharmaceutical composition, wherein the reservoir is operable to contain a quantity of the pharmaceutical composition, wherein the pharmaceutical composition includes an anti-muscarinic agent, wherein the anti-muscarinic agent is atropine or a pharmaceutically acceptable salt thereof, a cholinesterase reactivator, wherein the cholinesterase reactivator is 2-pyridine aldoxime methyl chloride, a vasoactive agent, wherein the vasoactive agent is epinephrine or a pharmaceutically acceptable salt thereof, and an anti-convulsant agent, wherein the anti-convulsant agent is diazepam or a pharmaceutically acceptable salt thereof. In one embodiment, the pharmaceutical composition provides a dose of about 0.1 mg to about 10 mg of the atropine or the pharmaceutically acceptable salt thereof, about 1 mg to about 1000 mg of the 2-pyridine aldoxime methyl chloride, about 0.01 mg to about 10 mg of the epinephrine or the pharmaceutically acceptable salt thereof, and about 0.1 mg to about 20 mg of the diazepam or the pharmaceutically acceptable salt thereof.

In yet another embodiment, the present invention provides a device for intranasal administration of a pharmaceutical composition including a reservoir and a means for discharging one or more doses of the pharmaceutical composition, wherein the reservoir is operable to contain a quantity of the pharmaceutical composition, wherein the pharmaceutical composition includes an anti-muscarinic agent, wherein the anti-muscarinic agent is atropine or a pharmaceutically acceptable salt thereof, a cholinesterase reactivator, wherein the cholinesterase reactivator is 2-pyridine aldoxime methyl chloride, a vasoactive agent, wherein the vasoactive agent is epinephrine or a pharmaceutically acceptable salt thereof, an anti-convulsant agent, wherein the anti-convulsant agent is diazepam or a pharmaceutically acceptable salt thereof, a vasodilator, wherein the vasodilator is phentolamine or a pharmaceutically acceptable salt thereof, and a carrier.

These and other aspects of the present invention will become apparent to those skilled in the art after a reading of the following description of the preferred embodiment when considered with the drawings, as they support the claimed invention.

DETAILED DESCRIPTION

Figure 1:
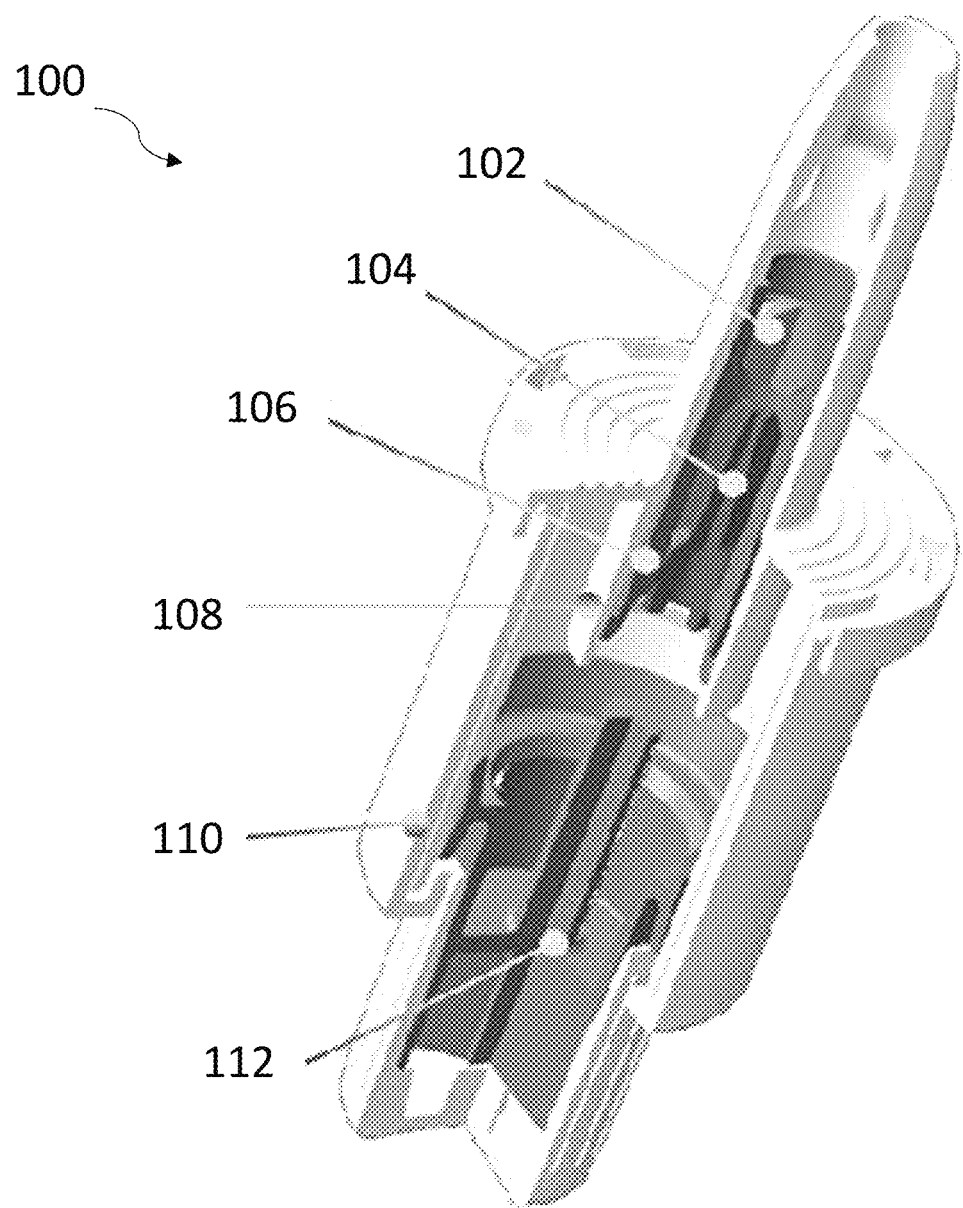
FIG. 1 illustrates one embodiment of a nasal delivery device according to the present invention.

The present invention is generally directed to systems to counteract the medical complications associated with organophosphate exposure (e.g., due to chemical warfare, such as nerve agents) including clinical toxicity associated with acetylcholine excess which may include respiratory failure, bronchoconstriction, hypotensive shock, bradycardia, hypertension, seizures, cardiac arrest, or other situations requiring the need to implement cardiopulmonary resuscitation (CPR) and/or basic or advanced cardiac life support (ACLS). Disclosed herein are dry powder compositions and unit doses that include vasoactive and non-vasoactive agents (e.g., atropine, pralidoxime chloride, epinephrine, and/or diazepam) suitable for intranasal administration, methods of making the compositions, delivery devices and packaging to improve their effectiveness in emergency treatment settings, and methods of using the compositions to treat the effects of exposure to organophosphate agents.

In one embodiment, the present invention provides a device for intranasal administration of a pharmaceutical composition including a reservoir and a means for discharging one or more doses of the pharmaceutical composition, wherein the reservoir is operable to contain a quantity of the pharmaceutical composition, wherein the pharmaceutical composition includes an anti-muscarinic agent, wherein the anti-muscarinic agent is atropine or a pharmaceutically acceptable salt thereof, a cholinesterase reactivator, wherein the cholinesterase reactivator is 2-pyridine aldoxime methyl chloride, a vasoactive agent, wherein the vasoactive agent is epinephrine or a pharmaceutically acceptable salt thereof, and an anti-convulsant agent, wherein the anti-convulsant agent is diazepam or a pharmaceutically acceptable salt thereof. In one embodiment, the pharmaceutical composition provides a dose of about 0.1 mg to about 10 mg of the atropine or the pharmaceutically acceptable salt thereof, about 1 mg to about 1000 mg of the 2-pyridine aldoxime methyl chloride, about 0.01 mg to about 10 mg of the epinephrine or the pharmaceutically acceptable salt thereof, and about 0.1 mg to about 20 mg of the diazepam or the pharmaceutically acceptable salt thereof. In one embodiment, the device includes a nasal probe, wherein the nasal probe is operable to be replaced between discharges. In one embodiment, the pharmaceutical composition further includes a vasodilator, wherein the vasodilator is phentolamine or a pharmaceutically acceptable salt thereof. In one embodiment, the pharmaceutical composition provides a dose of about 0.01 mg to about 10 mg of the phentolamine or the pharmaceutically acceptable salt thereof. In one embodiment, the pharmaceutical composition further includes a catechol-o-methyl transferase (COMT) inhibitor. In one embodiment, the COMT inhibitor is entacapone or a pharmaceutically acceptable salt thereof. In one embodiment, the pharmaceutical composition provides a dose of about 5 mg to about 200 mg of the entacapone or the pharmaceutically acceptable salt thereof. In one embodiment, the pharmaceutical composition further includes an anticaking agent. In one embodiment, the anticaking agent is tribasic calcium phosphate. In one embodiment, a median particle diameter of the atropine or the pharmaceutically acceptable salt thereof, the 2-pyridine aldoxime methyl chloride, the epinephrine or the pharmaceutically acceptable salt thereof, and/or the diazepam or the pharmaceutically acceptable salt thereof is about 30 μm. In one embodiment, the pharmaceutical composition further includes at least one antihistamine. In one embodiment, the pharmaceutical composition further includes at least one steroid. In one embodiment, the pharmaceutical composition further includes a carrier. In one embodiment, the carrier includes at least one cellulose and/or at least one starch. In one embodiment, the pharmaceutical composition further includes one or more agents selected from a group consisting of an excipient, a preservative, a humectant, a thickening agent, a solubilizing agent, a taste-masking agent, a scent-masking agent, an antioxidant enzyme, a viscosity enhancing agent, a dispersing agent, a surfactant, a chelator, a colorant, or any combination thereof. In one embodiment, the pharmaceutical composition further includes one or more agents selected from a group consisting of a mucosal permeation or penetration enhancer, a mucoadhesive, a mucosal transit slowing agent, a mucosal transport enhancer, or any combination thereof.

In another embodiment, the present invention provides a kit for intranasal administration of a pharmaceutical composition including at least one device, wherein each of the at least one device includes a reservoir and a means for discharging one or more doses of the pharmaceutical composition, wherein the reservoir is operable to contain a quantity of the pharmaceutical composition, wherein the pharmaceutical composition includes an anti-muscarinic agent, wherein the anti-muscarinic agent is atropine or a pharmaceutically acceptable salt thereof, a cholinesterase reactivator, wherein the cholinesterase reactivator is 2-pyridine aldoxime methyl chloride, a vasoactive agent, wherein the vasoactive agent is epinephrine or a pharmaceutically acceptable salt thereof, and an anti-convulsant agent, wherein the anti-convulsant agent is diazepam or a pharmaceutically acceptable salt thereof. In one embodiment, the pharmaceutical composition provides a dose of about 0.1 mg to about 10 mg of the atropine or the pharmaceutically acceptable salt thereof, about 1 mg to about 1000 mg of the 2-pyridine aldoxime methyl chloride, about 0.01 mg to about 10 mg of the epinephrine or the pharmaceutically acceptable salt thereof, and about 0.1 mg to about 20 mg of the diazepam or the pharmaceutically acceptable salt thereof. In one embodiment, the at least one device is enclosed in a pouch or a hard case. In one embodiment, the pouch or the hard case is water resistant or waterproof. In one embodiment, the pouch or the hard case includes an exterior finish including a camouflage. In one embodiment, the pouch and/or the hard case is MOLLE-compatible.

In yet another embodiment, the present invention provides a device for intranasal administration of a pharmaceutical composition including a reservoir and a means for discharging one or more doses of the pharmaceutical composition, wherein the reservoir is operable to contain a quantity of the pharmaceutical composition, wherein the pharmaceutical composition includes an anti-muscarinic agent, wherein the anti-muscarinic agent is atropine or a pharmaceutically acceptable salt thereof, a cholinesterase reactivator, wherein the cholinesterase reactivator is 2-pyridine aldoxime methyl chloride, a vasoactive agent, wherein the vasoactive agent is epinephrine or a pharmaceutically acceptable salt thereof, an anti-convulsant agent, wherein the anti-convulsant agent is diazepam or a pharmaceutically acceptable salt thereof, a vasodilator, wherein the vasodilator is phentolamine or a pharmaceutically acceptable salt thereof, and a carrier. In one embodiment, the pharmaceutical composition provides a dose of about 0.1 mg to about 10 mg of the atropine or the pharmaceutically acceptable salt thereof, about 1 mg to about 1000 mg of the 2-pyridine aldoxime methyl chloride, about 0.01 mg to about 10 mg of the epinephrine or the pharmaceutically acceptable salt thereof, about 0.1 mg to about 20 mg of the diazepam or the pharmaceutically acceptable salt thereof, and about 0.01 mg to about 10 mg of the phentolamine or the pharmaceutically acceptable salt thereof.

Organophosphorous (OP) compounds, including pesticides and most importantly chemical warfare nerve agents (CWNAs), are extremely lethal and (in the case of CWNAs) are easy to produce and disperse. The opportunity for rogue countries or terrorists to employ these agents as a weapon is of national concern. The current treatment approach for organophosphate exposure includes the administration of atropine in combination with the oxime acethycholinesterase (AChE) reactivator pralidoxime chloride (2-PAM) by intramuscular administration. See, e.g., (1) Agency for Toxic Substances and Disease Registry, 2011. Retrieved from http://www.atsdr.cdc.gov/MHMI/mmg166.pdf; (2) Bailey A M, et al., 2014, Adv Emerg Nurs J 36:22-33; and (3) Theirmann H, et al. 2011, Toxicol Lett 206; 77-83, each of which is incorporated herein by reference in its entirety.

Rapid delivery of these therapeutic drugs in a non-clinical setting has been challenging due to the reliance on injection of multiple drugs that are formulated as aqueous solutions. Limitations to this approach include limited absorption and stability issues. There practical disadvantages of storing and utilizing glass vials, liquid, and needles. Additionally, these compositions must be protected from light and heat. Effective administration of these compositions is further limited by the need for first responders or affected individuals to correctly utilize auto-injectors or deliver injection via syringe.

The present invention eliminates these restrictions and creates the ability for therapeutic treatments that are more robust and able to be effectively delivered to individuals or affected groups. The present invention widens the ability to deploy, store, or pre-position these treatments in a range of environmental conditions and also reduce the skills needed to utilize the treatments by first responders or the affected individuals.

Chemical Warfare Nerve Agents and Organophosphate Type Pesticides

Nerve agents and organophosphate pesticides act through modulating the transmission and breakdown of acetylcholine. There are two main categories of nerve agents, which are classified as either G or V agents (see Table 1). Each category differentiates agents based on physical and chemical characteristics. For example, in the case of sarin (isopropyl methylphosphonofluroidate), this G type agent is easy to produce and disperse. Rogue countries or terrorists are easily able to employ sarin as a weapon. CWNAs are absorbed through all routes. Ingestion and inhalation lead to immediate onset of symptoms if vaporized or misted.

TABLE 1

| Nerve Agents | |
|---|---|
| G Agents | V Agents |
| Sarin (GB) | VX |
| Cyclosarin (GF) | VR |
| Soman (GD) | |
| Tabun (GA) | |

The basic structure for organophosphates is shown below.

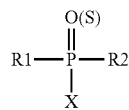

Each organophosphate molecule contains a phosphoryl or thiophosphoryl group, two side chains (R1, R2), and a leaving group (X).

Pathophysiology and Clinical Manifestation

Chemical warfare nerve agents and organophosphates work, in part, through irreversible inhibition of acetylcholinesterase, which affects the circulatory, respiratory, and neurological systems. This inhibition of acetylcholinesterase leads to accumulation of acetylcholine. Acetylcholine acts upon two receptor subtypes: the muscarinic receptors and the nicotinic receptors. Each receptor is operable to mediate different adverse effects from acetylcholine excess (Table 2). For example, muscarinic effects are operable to include bradycardia and bronchospasm, and nicotinic effects are operable to result in weakness. Most fatalities result from acute respiratory failure, which presents the opportunity for treatment. In addition, hypotension often occurs, which is operable to be secondary to decreased sympathetic outflow from the medulla (sympatholysis). Vasoactive agents (e.g., epinephrine) are useful in these situations and where cardiorespiratory support is needed. Benzodiazepines (e.g., diazepam) are useful for seizure prevention and control if needed.

TABLE 2

| Clinical effects of organophosphate exposure | |
|---|---|
| Anatomic Site of Action | Signs and Symptoms |
| Muscarinic effects | |
| Sweat glands | Sweating |
| Pupils | Constricted pupils |
| Lacrimal glands | Lacrimation |
| Salivary glands | Excessive salivation |
| Bronchial tree | Wheezing |
| Gastrointestinal | Cramps, vomiting, diarrhea, tenesmus |
| Cardiovascular | Bradycardia, decrease in blood pressure |
| Ciliary body | Blurred vision |
| Bladder | Urinary incontinence |

TABLE 2-continued

| Clinical effects of organophosphate exposure | |
|---|---|
| Anatomic Site of Action | Signs and Symptoms |
| Nicotinic effects | |
| Striated muscle | Fasciculations, cramps, weakness, twitching, paralysis, respiratory embarrassment, cyanosis, arrest |
| Sympathetic ganglia | Tachycardia, elevated blood pressure |
| Central nervous system effects depression | Anxiety, restlessness, ataxia, convulsions, insomnia, coma, absent reflexes, Cheyne-Stokes respirations, respiratory and circulatory |

Activation of the muscarinic receptors results in series of symptoms that are operable to be referred to by the mnemonic DUMBELS: diaphoresis and diarrhea, urination, miosis, bronchorrhea and bronchospasm, emesis, lacrimation, salivation, and secretion. The most critical aspect related to chemical exposure is respiratory failure, which is highlighted by bronchorrhea and bronchoconstriction, and is operable to result in life-threatening pulmonary edema. Respiratory failure is the leading cause of death from nerve agents.

Activation of the nicotinic receptors is operable to lead to several symptoms as highlighted in Table 2 and includes significant effects on the cardiovascular system. These effects are operable to include bradycardia and hypotension. These cardiovascular effects are also operable to contribute to death.

Therapeutic Approach

The most critical initial approach to the management of nerve agent or organophosphate exposure is limiting bronchorrhea associated with muscarinic activation, which is operable to lead to death. In addition, reactivating acetylcholinesterase is a priority. The two primary agents to address these priorities are atropine and pralidoxime (2-PAM). Atropine's role is as an antimuscarinic agent that attenuates the bronchorrhea associated symptoms. Atropine competes with acetylcholine at the muscarinic receptor. Atropine is titrated until secretions are limited and breathing is improved. Multiple doses, including intravenous administration, may be required. Other agents (e.g., glycopyrrolate, which is also an antimuscarinic agent) are also operable to be considered if atropine is not available.

Atropine does not affect the nicotinic receptors and cannot reactivate acetylcholinesterase. In addition, it does not treat symptoms associated with the effects on nicotinic receptors. To treat the effect of nerve agents on nicotinic receptors, a cholinesterase reactivator agent (e.g., pralidoxime (monopyridinium oxime pralidoxime—2-PAM)) is required. Pralidoxime is effective in reversing nicotinic symptoms and is operable to reactivate acetylcholinesterase. In reactivating acetylcholinesterase, cholinergic neural function is operable to normalize. From a clinical perspective, 2-PAM is operable to help relieve respiratory muscle paralysis and has some minor antimuscarinic effects.

If a patient is to survive exposure to a nerve agent, effective administration of both atropine and 2-PAM is required. In addition, other therapeutic approaches including assisted ventilation, phentolamine, diazepam, and/or epinephrine are operable to be needed as shown in Table 3.

TABLE 3

Recommendations for nerve agent therapy-prehospital management Antidotes

| Patient's age | Mild/Moderate Symptoms | Severe Symptoms | Other treatment |
| --- | --- | --- | --- |
| Infant (0-2 years) | Atropine: 0.05 mg/kg IM; 2-PAM Cl: 15 mg/kg IM | Atropine: 0.1 mg/kg IM; 2-PAM Cl: 25 mg/kg IM | Assisted ventilation should be started |
| Child (2-10 years) | Atropine: 1 mg IM; 2-PAM Cl: 15 mg/kg IM | Atropine: 2 mg IM; 2-PAM Cl: 25 mg/kg IM | after administration of antidotes for extreme exposures. |
| Adolescent (older than 10 years) | Atropine: 2 mg IM; 2-PAM Cl: 15 mg/kg IM | Atropine: 4 mg IM; 2-PAM Cl: 25 mg/kg IM | Repeat atropine (2 mg IM) at 5- to 10-min intervals until |
| Adult | Atropine: 2-4 mg IM; 2-PAM Cl: 600 mg IM | Atropine: 6 mg IM; 2-PAM Cl: 1800 mg IM | secretions have diminished and |
| Elderly, frail | Atropine: 1 mg IM; 2-PAM Cl: 10 mg/kg IM | Atropine: 2-4 mg IM; 2-PAM Cl: 25 mg/kg IM | breathing is comfortable or airway resistance has returned to near normal. |

See, e.g., (1) Advanced Emergency Nursing Journal Medical 2014; 36:22-33 and (2) Management Guidelines for Nerve Agents: Tabun (GA); Sarin (GB); Soman (GD); and VX," by Agency for Toxic Substances and Disease Registry, 2011. Retrieved from http://www.atsdr.cdc.gov/MHMI/mmg166.pdf, each of which is incorporated herein by reference in its entirety.

Dosage Delivery

Atropine and 2-PAM are operable in the prior art to be delivered either by an intramuscular (IM) or an intravenous (IV) route of administration. In the field, the most convenient and easily accessible route of administration is IM. A prefilled autoinjector (DUODOTE®) is currently available that contains 2.1 mg of atropine and 600 mg of pralidoxime chloride. DUODOTE® is indicated for the treatment of poisoning by organophosphorous nerve agents and insecticides. A total of up to 3 DUODOTE® injections into the patient's mid-lateral thigh are operable to be administered to patients with severe symptoms. Once the patient is hospitalized, both atropine and 2-PAM are operable to continue to be given by the IM route or by IV administration.

Drawbacks of WI Injection for Delivery of Primary and Secondary Treatments

Delivery of atropine, 2-PAM, epinephrine, and/or diazepam via injection has a number of potential drawbacks. Untrained personnel may make mistakes in the use of autoinjectors, including administration in an incorrect site and failure to hold the device against the patient's thigh for ten seconds after activation. Additional concerns are accidental needle sticks and sharps disposal. The needle length may be inadequate to reach the muscle in obese individuals, which may result in a suboptimal level of drug delivered. Another drawback is the requirement to store these devices in a narrow range of temperature because aqueous compositions are known to degrade under high temperature conditions. The DUODOTE® autoinjector, as an example, must be stored within a temperature range of 15 to 30 degrees Celsius. These storage requirements may limit the practical availability of the drug under field conditions or require special facilities for storage for civil defense application.

Atropine has been shown to undergo rapid degradation when exposed to heat. A recent study for the US National Park Service medical program found that among eight injectable drugs tested, "Atropine had the most degradation, being undetectable after 4 weeks of heat exposure." See Patil Armenian, Danielle Campagne, Geoff Stroh, Crystal Ives Tallman, William Z. D. Zeng, Thomas Lin & Roy R. Gerona (2017) Hot and Cold Drugs: National Park Service Medication Stability at the Extremes of Temperature, Prehospital Emergency Care, 21:3, 378-385, DOI: 10.1080/10903127.2016.1258098, which is incorporated herein by reference in its entirety.

Another concern is that systemic administration of 2-PAM does not readily reach across the blood brain barrier (BBB) and into the central nervous system (CNS) to achieve maximum treatment success. On the other hand, nasal delivery allows for increased levels of 2-PAM into the CNS. Recent literature has demonstrated that nasal delivery of compounds and drugs that do not significantly cross the BBB when given orally, WI, or IV achieve potentially therapeutic concentrations in the CNS via nasal delivery. Advantageously, giving 2-PAM by nasal delivery is operable to have similar or greater therapeutic efficacy as WI, and potentially at a much lower dose. Nasal delivery of 2-PAM offers a distinct advantage over traditional methods. See, e.g., (1) Crowe T P, et al. Life Sciences 2018; 195:44-52; (2) Ganger S, et al. Pharmaceutics 2018; 10:1-28 doi:10.3390; and (3) Pashirova T N, et al. Colloids and Surfaces B: Biointerfaces 2018; 171:358-367, each of which is incorporated herein by reference in its entirety.

Potential Benefits of Nasal Delivery for Primary Treatment and Secondary Treatments The present invention addresses the recomposition of drugs used to treat chemical agent exposure and organophosphate exposure as a means to make them more practical to effectively deliver when treating individuals and groups in an emergency situation. During active engagement in a hostile environment or in a public attack involving mass number of casualties it is important to have simple options for effective treatment. A novel approach to effective drug delivery is by nasal delivery.

The role for nasal route of drug delivery has greatly expanded over the last decade and includes a wide spectrum of drugs. Currently marketed nasally delivered drugs include: Butorphanol (Stadol NS Nasal Spray, Bristol Myers Squibb Co., USA), calcitonin (Miacalcin Nasal Spray, Novartis), dihydroergotamine (Migranal Nasal Spray, Novartis, Inc.), sumatriptan (Imitrex Nasal Spray, GlaxoSmithKline), and desmopressin (DDAVP Nasal Spray, Aventis Pharma, USA). Cromolyn sodium (Nasal-crom Nasal Solution, Fisons Pharmaceuticals) is available in a solution form. Budesonide (Rhinocort Nasal Inhaler, Astra) and beclomethasone diproprionate (Rino Clenil, Chiesi Farmaceutici) are marketed in the form of metered-dose pressurized aerosols. Beclomethasone diproprionate is also available in the form of a metered-dose manual spray unit (Beconase AQ, Glaxo-SmithKline, and Vancenase AQ, Schering Plough Corporation). Recently, several nasally delivered drugs have been introduced for utilization in "rescue" or emergency situations. These include naloxone for treatment of opioid overdose and glucose for severe hypoglycemia (New Drug Application (NDA) filed). In the case of naloxone, the availability of a nasal delivery dose form as an alternative to injection has rapidly expanded patient and first responder access to the therapy and usage of this drug. See, e.g., Verma R K et al. 2001 Pharmaceutical Technology On-Line 25(2): 1-14, which is incorporated herein by reference in its entirety.

Combination of Primary Treatment and Secondary Condition Treatment

In one aspect, the present invention combines at least two drugs used for primary treatment of chemical agent exposures with one or more third drug used for secondary treatment of exposures in a combined, powder composition that is operable to be delivered nasally. In certain embodiments, the delivery device includes the two primary treatment drugs in a powder composition with at least one enabling agent and/or at least one carrier and/or excipient. In certain embodiments, the secondary treatment drug(s) are provided separately (e.g., in a separate delivery device) in a powder composition with at least one enabling agent and/or at least one carrier and/or excipient. This invention includes pharmaceutical compositions that include these primary treatment drugs and secondary treatment drugs, nasal delivery devices including these compositions, packaging for these compositions to improve their effectiveness in emergency treatment settings, and methods for their use.

One aspect of the invention is the novel combination including atropine, 2-PAM, epinephrine, and/or diazepam. By utilizing a dry powder composition, it becomes possible to combine the therapeutic treatments for both primary and secondary effects of nerve agent exposure, which may lead to both morbidity and mortality after exposure. In essence, four distinct therapies are operable to be required to decrease morbidity and mortality following exposure to a nerve agent. The most critical initial approach to the management of nerve agent exposure is limiting bronchorrhea associated with muscarinic activation, the effect on nicotinic receptors, and reactivating acetylcholinesterase.

Following exposure to a nerve agent there are both primary and secondary physiological effects that must be addressed. Primary physiological effects of the nerve agent are based on irreversible inhibition of acetylcholinesterase, which affects the circulatory, respiratory, and neurological systems. This inhibition of acetylcholinesterase leads to accumulation of acetylcholine. As previously described, acetylcholine acts upon two receptor subtypes: the muscarinic receptors and the nicotinic receptors. Each receptor is operable to mediate different adverse effects from acetylcholine excess (Table 2). For example, muscarinic effects are operable to include bradycardia and bronchospasm, and nicotinic effects are operable to result in weakness. Most fatalities result from acute respiratory failure, which presents the opportunity for treatment. In addition, hypotension is often operable to occur, and may be secondary to decreased sympathetic outflow from the medulla (sympatholysis).

In addition to treating the primary physiological effects associated with the exposure to a nerve agent, there are also secondary conditions to address. These conditions include bronchoconstriction, hypotension, bradycardia, and potentially cardiac arrest. The preferred treatment for these effects is epinephrine, which is typically delivered via IV or IM injection. Including epinephrine as part of the medical approach to treating patients exposed to a nerve agent is critical. One effect of exposure to a nerve agent is bronchoconstriction leading to respiratory failure and death. Epinephrine through activation of beta-2 receptors is operable to help reverse bronchoconstriction. Another secondary condition to address is seizures. The preferred treatment for these effects is administration of benzodiazepines (e.g., diazepam), which is typically delivered by IV or IM injection.

Following exposure to a nerve agent bronchoconstriction, hypotension, bradycardia, cardiac arrest, and seizures may also occur. To address these potential physiological effects, administration of a third agent (e.g., epinephrine) and/or a fourth agent (e.g., diazepam) needs to be considered. Given the potential need to administer all four agents (atropine, 2-PAM, epinephrine, and diazepam), combining all four agents or other combinations involving two or three drugs into one delivery device has significant advantages when time is of the essence.

A primary advantage of combining these therapies in a single delivery device is the reduced complexity of skills and decision-making required, and reduced time needed, to effect treatment in field conditions or a situation involving mass casualties. Additional advantages of combining multiple agents into a single powder nasal composition as compared to IV, IM, or SQ include:

- The nasal dry powder device is easier to use and is operable to be administered by untrained personnel and easily administered by troops or first responders in the field.
- The nasal device has a substantially smaller form factor—making it easier to incorporate in field kits and easier for an individual to carry at all times.
- There are no needles, glass, or aqueous dosage forms.
- When a multi-dose device is employed, with no needle and injection involved, the same device is operable to be used to treat two or more individuals.
- The nasal dry powder compositions as described herein are a more stable product and operable to withstand a wider range of environmental conditions than the conventional aqueous preparations.

Primary Treatment

The compositions and/or unit doses disclosed herein describe nasal compositions for atropine and 2-PAM. The dry powder compositions permit effective delivery in a stable and convenient environment. In addition, the composition is operable to include one or more enabling agents including, but not limited to, mucoadhesives, mucosal transit slowing agents, modern permeation enhancers, and/or other pharmaceutically acceptable excipients that are non-toxic to nasal tissues. Addition of suitable enabling agents to the dry powder compositions and/or unit doses is surprisingly operable to aid in muco-adhesion, dissolution, and absorption.

Secondary Treatments (Epinephrine)

In addition to treating the primary medical effects associated with the exposure to a nerve agent, there are also secondary conditions to address. These conditions include bronchoconstriction, hypotension, bradycardia, and potentially cardiac arrest.

As in the aforementioned case of primary treatments, there is a need, especially in the field setting, to have an easily administered and convenient method for drug delivery to treat these secondary conditions. One approach for drug delivery is the nasal administration of drugs such as epinephrine and diazepam.

The nasal dry powder composition is a more stable product and is operable to withstand a wider range of environmental conditions than the conventional aqueous preparations. The preferred treatment for these effects includes epinephrine, which is typically delivered via IV or IM injection. Including epinephrine as part of the medical approach to treating patients exposed to a nerve agent is critical. One of the effects of exposure to a nerve agent is bronchoconstriction, leading to respiratory failure and death. Epinephrine through activation of beta-2 receptors is operable to help reverse bronchoconstriction.

Previous animal studies have demonstrated that intranasal delivery of epinephrine solution is operable to be an effective route of drug administration during cardiac arrest. See, e.g., (1) Bleske B E et al. 1992 Ann Emerg Med 21(9):1125-1130; (2) Bleske B E et al. 1996 Am J Emerg Med 14:133-138; and (3) Bleske B E et al. 1996 Pharmacother 16(6): 1039-1045, each of which is incorporated herein by reference in its entirety. Although these authors observed a dose response, the absolute bioavailability appeared to be quite low, despite the use of 1% taurodeoxycholic acid solution (bile salts), which is now known to be a damaging mucosal permeation enhancer. Moreover, to minimize the severe local vasoconstriction caused by epinephrine that could potentially limit the mucosal absorption of epinephrine, they used pretreatment with intranasal phentolamine. The phentolamine pretreatment was administered 1 min prior to intranasal epinephrine dosing to enhance epinephrine absorption. To prevent its local degradation on the external nasal mucosa, the investigators used large loading doses of phentolamine ranging from 0.25 to 2.5 mg/kg/nostril, which amount to 15 mg for a dog weighing 21 kg. The loading doses of epinephrine studied were 0.075, 0.75, and 7.5 mg/kg/nostril, which amount to 157 mg/nostril for a dog weighing 21 kg. The greatest cardiac effects and the greatest epinephrine plasma concentrations of about ~1,400 ng/mL were observed at 0.25 mg/kg/nostril of phentolamine and 7.5 mg/kg/nostril of epinephrine. For desired treatment the authors used 7.5 mg/kg/nostril of epinephrine with 1% taurodeoxycholic acid as a permeation enhancer after pretreatment with 0.75 mg/kg/nostril in about 1 mL each application.

Although this study revealed the systemic delivery of aqueous epinephrine by the nasal route of administration, it had significant limitations for translation into clinical practice, including: (i) dosing that was not optimized (it is also unclear whether phentolamine was used at its lowest level with no or minimal systemic exposure, which would have competed with epinephrine actions); (ii) the staged predosing of phentolamine followed by epinephrine, which is totally impractical for real-world emergency treatment; (iii) the use of a very large loading dose of epinephrine (157 mg/nostril for a dog weighing 21 kg) and vasodilator (15 mg/nostril for a dog weighing 21 kg); (iv) use of large volumes (e.g., 1.0 mL) of solution per nostril and even at that volume, the epinephrine crystallized out (this large volume in each nostril is also impractical for modern nasal aqueous sprays, which use only 100-250 μL volume, and even at this lower volume quite a significant percentage of the aqueous dose slides off the more dense nasal mucosa and is swallowed); and (v) the use of bile salts as mucosal permeation enhancers caused severe nasal mucosal tissue damage, and raises the question to what extent the systemic delivery was achieved due to the destruction of this tissue barrier, rather than by the actual penetration by epinephrine. This safety aspect of the study was a fatal flaw for clinical translation of this technology. This technology is dormant with no follow-up studies since 1996.

An inhaled epinephrine composition that is delivered to the lungs of a subject and administered by breath-activated devices is described in U.S. Pat. Nos. 7,954,491 and 7,947,742. However, such delivery of epinephrine is not feasible in persons already in cardiac arrest because they are unable to breathe. Also, as inferred by the Bleske et al. 1996 study, any epinephrine composition that does not include other epinephrine-enabling agents (e.g., a vasodilator) will not be effective to counter the cardiac shock within the typical 1-5 minutes needed for rescue of cardiac arrest. Additionally, in a recent study by Nakponetong, a nasal spray of a high loading dose of epinephrine (5 mg) without any other enabling agents was given to normal human subjects vs. intramuscular epinephrine, and had a time to peak plasma concentration ($T_{max}$) in 70±17 minutes. A $T_{max}$ of 70±17 minutes, even at the higher loading dose of epinephrine, is insufficient to be of any utility in cardiac arrest. A $T_{max}$ of 1-5 minutes is considered critical for treating cardiac arrest. See, e.g., Nakponetong et al. 2010 J. Allergy Clin. Immunol. 125(2): Abstract 859, which is incorporated herein by reference in its entirety.

Hence, despite the theoretical promise for the intranasal route for delivering epinephrine, there is a need for improving the intranasal (IN) epinephrine composition for the treatment of cardiac arrest and other conditions, such as hypotension and severe bradycardia. As noted above, the investigation by Bleske B. E. et al. 1996 also had a number of significant practical limitations that prevented their clinical translation.

The compositions and/or unit doses disclosed herein however have solved critical limitations of the above-mentioned references. The dry powder epinephrine compositions permit lowering the loading dose of epinephrine by the optional addition of a topically acting vasodilator (e.g., phentolamine) at the same time in the same dose. In addition to epinephrine and vasodilator, the present composition is operable to include one or more enabling agents including, but not limited to, mucoadhesives, mucosal transit slowing agents, modern permeation enhancers, and/or other pharmaceutically acceptable excipients that are non-toxic to nasal tissues. Addition of suitable enabling agents to the dry powder compositions and/or unit doses is surprisingly operable to aid in muco-adhesion, dissolution, and absorption.

Herein, the resulting nasal route of administration to achieve therapeutic doses sufficient to manage or reverse nerve agent induced bronchoconstriction, hypotension, bradycardia, cardiac arrest, or coronary arrest is: (i) rapid; (ii) operable to be administered by non-professionals; and (iii) operable to use practical doses of an intranasal composition including a vasoactive agent (e.g., epinephrine), a vasodilator, a catechol-o-methyl transferase (COMT) inhibitor, mucosal transit slowing agents, and modern permeation enhancers that are not toxic to nasal tissues.

As mentioned, another consideration for the use of intranasal epinephrine is in the setting of severe hypotension (hypotensive shock) secondary to a number of causes including, exposure to a nerve agent, trauma, hypovolemia, severe bradycardia, or septic shock, where intravenous access is not readily available in a timely fashion. One setting where intranasal epinephrine is valuable is during active combat. Administering nasal epinephrine in the battlefield to help maintain blood pressure is practical given the ease of administration by the nasal route. As previously discussed, epinephrine is an ideal candidate to help raise systolic pressures given that epinephrine is a potent vasoconstrictor through the activation of mainly alpha-1 receptors. In addition, previous studies as cited above have shown the proof of concept that nasal epinephrine is operable to be effectively given by nasal route and achieve therapeutic levels to raise pressure even during cardiac arrests.

Herein, the resulting nasal route of administration to achieve therapeutic doses sufficient to manage or reverse hypotensive shock is: (i) rapid; (ii) operable to be administered by non-professionals; and (iii) operable to use practical doses of an intranasal composition including various combinations of one or more of a vasoactive agent (e.g., epinephrine), a vasodilator, a COMT inhibitor, mucosal transit slowing agents, and modern permeation enhancers that are not toxic to nasal tissues.

In fact, there is recent study in animals demonstrating that the administration of subcutaneous epinephrine following exposure to sarin is operable to improve mortality. See, e.g., Gundavarapu S, et al. Toxicology and Applied Pharmacology 2014; 274:200-208, which is incorporated herein by reference in its entirety. Advantageously, administering epinephrine by nasal route as in the present invention provides for greater and more consistent epinephrine levels and is easier to administer than IM or SQ. In addition to treating bronchoconstriction, epinephrine is also vital for the treatment of hypotension, bradycardia, and cardiac arrest, all of which are operable to occur following exposure to a nerve agent. Therefore, there is a critical need to provide a simple and effective delivery system for the administration of epinephrine following a nerve agent attack. Advantageously, the present invention provides nasal delivery of the administration of epinephrine following a nerve agent attack.

Secondary Treatment (Benzodiazepines)

Another secondary medical condition that occurs after exposure to a nerve agent is seizures. The preferred treatment is the administration of benzodiazepines, which are typically delivered via IV or IM injection. Including administration of a benzodiazepine as part of the medical approach to treating patients exposed to a nerve agent is critical. The mechanism for increased seizure activity following exposure is not entirely understood. Proposed mechanisms include secondary increase in acetylcholine levels and glutamate release. Blockade of gamma-aminobutyric acid (GABA) receptors may also play a role. Given the difficult nature of treating nerve agent induce seizures and the likely role of GABA, the use of benzodiazepines (e.g., diazepam, lorazepam, midazolam) with their effect on increasing GABA activity are drugs of choice. Therefore, there is a critical need to provide a simple and effective delivery system for the administration of benzodiazepines following a nerve agent attack. Advantageously, the present invention provides nasal delivery of the administration of benzodiazepines following a nerve agent attack.

As in the aforementioned case of primary treatments, there is a need, especially in the field setting, to have an easily administered and convenient method for drug delivery to treat this secondary condition. One approach for drug delivery is the nasal administration of drugs such as diazepam or other type of benzodiazepines, which are considered a standard of care for acute treatment and prevention of seizures.

There is a long-felt, unmet need for intranasal dry powder compositions, unit doses, and kits to be used in response to organophosphate exposure. None of the prior art includes intranasal dry powder compositions, unit doses, and kits to be used in response to organophosphate exposure. The intranasal dry powder compositions of the present invention preferably do not include a preservative. Additionally, the delivery devices of the present invention preferably do not require a propellant.

Compositions

Disclosed herein are intranasal dry powder compositions and/or unit doses to be used, for example and not limitation, in treatment of chemical attacks or exposure to nerve agents. Further, disclosed herein are intranasal dry powder compositions and/or unit doses including at least one active pharmaceutical ingredient. The at least one active pharmaceutical ingredient includes, but is not limited to, (i) an anticholinergic agent (e.g., atropine), (ii) a cholinesterase reactivator agent (e.g., monopyridinium oxime pralidoxime), (iii) a vasoactive agent (e.g., epinephrine), and/or (iv) an anticonvulsive agent (e.g., diazepam). The intranasal dry powder compositions and/or unit doses are further operable to include at least one enabling agent and/or at least on carrier and/or excipient.

Anticholinergic Agent

In one aspect, provided herein is an intranasal dry powder composition including an anticholinergic agent. In some embodiments, the anticholinergic is atropine or a pharmaceutically acceptable salt thereof. In some embodiments, the anticholinergic agent is scopolamine, benztropine, oxybutynin, tolterodine, tiotropium, oxitropium, and/or other agents with anticholinergic activity or anti-muscarinic activity (e.g., glycopyrrolate) or a pharmaceutically acceptable salt thereof. In a preferred embodiment, the anticholinergic agent is atropine or a pharmaceutically acceptable salt thereof. In some embodiments, a single dose of the anticholinergic agent is about 0.01 mg to about 10 mg. In another aspect, the amount of the anticholinergic agent (e.g., atropine) is at least about: 0.01 mg, 0.05 mg, 1.0 mg, 2.0 mg, 5.0 mg, or 10 mg in the compositions. In some embodiments, the anticholinergic agent (e.g., atropine) present in the compositions is about: 0.01 mg to 0.05 mg, 0.05 mg to 0.75 mg, 0.75 mg to 1.5 mg, 1.5 mg to 3.0 mg, 3.0 to 4.5 mg, 4.5 to 6.0 mg, 6.0 to 7.5 mg, 7.5 to 9.0 mg, or 9.0 to 10.0 mg. In some embodiments, the amount of an atropine agent (e.g., atropine) is about: 0.15, 0.3, 0.5, 0.75, 1, 1.5, 2, 3, 4, 5, 6, 7, 8, 9, or 10 mg in the compositions. In one instance, a single dose of the anticholinergic agent is about 0.75 mg. In one instance, a single dose of the anticholinergic agent is about 1.5 mg. In another instance, a single dose of the anticholinergic agent is about 3.0 mg. In another related aspect, the dose of the anticholinergic agent (e.g., atropine) is adjusted according to the weight of the patient at an increment of at least 0.01 mg/kg, or one wherein the dose is operable to be repeated a number of times if the patient failed to improve patient symptoms. In some embodiments, the composition, in the form of a single dose, includes about 0.01 mg to about 10 mg of anticholinergic agent. In some embodiments, the composition, in the form of a single dose, includes about 0.75 mg, 1.5 mg, or 3.0 mg of the anticholinergic agent.

In one embodiment, a unit dosage herein is operable to range from about 0.01 mg to about 1 mg, for example about: 0.1, 0.2, 0.3, 0.4, 0.5, 0.6, 0.7, 0.8, 0.9, or 1 mg of a composition. A unit dosage is also operable to be at least about: 0.01, 0.1, 0.5, or 1 mg of a composition. Administration of the compositions herein are operable to be repeated, e.g., every 5-20 minutes as necessary.

In some embodiments, the anticholinergic agent is about 0.005% to about 50% w/w of the weight of the composition, for example about: 0.005%, 0.01%, 0.05%, 0.1%, 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w based on the weight of the compositions and/or unit doses. For example, the anticholinergic agent is operable to be about 2.5%, about 4%, about 7.5%, or about 15% w/w of the composition. In some embodiments, the anticholinergic agent (e.g., atropine) is operable to be present in an amount of at least about: 0.25% w/w, 1% w/w, 5% w/w, 10% w/w, 20% w/w, 30% w/w, 40% w/w, or 50% w/w based on the weight of the compositions and/or unit doses. In some embodiments, the anticholinergic agent (e.g., atropine) is operable to be present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the compositions and/or unit doses.

In one embodiment, the dry powder compositions herein are operable to increase the maximal blood concentration ($C_{max}$) of the anticholinergic agent (e.g., atropine) to about 13 ng/mL. In one embodiment, the dry powder compositions herein are operable to increase the blood concentration of the anticholinergic agent (e.g., atropine) by about 1, 2, 3, 4, 5, 6, 7, 8, 9, 10, 11, 12, 13, 14, 15, 25, or 50 ng/mL.

In some embodiments, the dry powder composition disclosed herein, when administered to a patient, reaches a maximal blood concentration of the anticholinergic agent (e.g., atropine) in less than about 60 minutes ($T_{max}$) after administration. In some embodiments, the dry powder composition, when administered to a patient, reaches a maximal blood concentration ($T_{max}$) of the anticholinergic agent in less than about 60, 50, 40, 30, 20, 15, 10, 5, or 3 minutes ($T_{max}$) after administration. In one embodiment, the dry powder composition, when administered to a patient, reaches a maximal blood concentration ($T_{max}$) of the anticholinergic agent in less than about 30 minutes after administration. In some embodiments, the dry powder composition, when administered to a patient, reaches a mean area under the curve $(AUC)_{(0-180\ minutes)}$ of the anticholinergic agent which is at least 20%, 30%, 40% 50%, 60%, 70%, 80%, 90%, 100%, 110%, 120%, 130%, 140%, or 150% of the mean $AUC_{(0-180\ minutes)}$ of an equivalent IV, IM, or SQ injected anticholinergic agent. In some embodiments, the dry powder composition, when administered to a patient, reaches a mean $AUC_{(0-\infty)}$ of the anticholinergic agent that is at least 20%, 30%, 40% 50%, 60%, 70%, 80%, 90%, 100%, 110%, 120%, 130%, 140%, or 150% of the mean $AUC_{(0-\infty)}$ of an equivalent IV, IM, or SQ injected anticholinergic agent. In some embodiments, the equivalent IV, IM, or SQ injected anticholinergic agent includes 1 mg, 2 mg, 2.1 mg, 3 mg, 4 mg, 5 mg, 6 mg, 7 mg, 8 mg, 9 mg, or 10 mg of the anticholinergic agent. For example, the dry powder composition, when administered to a patient, reaches a mean $AUC_{(0-180\ minutes)}$ of the anticholinergic agent that is at least 80% of the mean $AUC_{(0-180\ minutes)}$ of a 2.1 mg IM injected anticholinergic agent. In another instance, the dry powder composition, when administered to a patient, reaches a mean $AUC_{(0-\infty)}$ of the anticholinergic agent that is at least 80% of the mean $AUC_{(0-\infty)}$ of a 2.1 mg IM injected anticholinergic agent.

In certain embodiments, the intranasal dry powder compositions and/or unit doses herein are operable to raise the blood concentration of the anticholinergic agent (e.g., atropine) to about 13 ng/mL within about 3 to about 60 minutes (e.g., about: 60, 50, 40, 30, 20, 15, 10, 5, or 3 minutes) or about 10 to about 15 minutes (e.g., about: 10, 11, 12, 13, 14, or 15 minutes) of intranasal administration. In one embodiment, the compositions herein increase the blood concentration of the anticholinergic agent (e.g., atropine) by about 13 ng/mL (e.g., 8 or 10 ng/mL) in about 10 to about 15 minutes (e.g., about: 10, 11, 12, 13, 14, or 15 minutes) or about 3 to about 60 minutes (e.g., about: 60, 50, 40, 30, 20, 15, 10, 5, or 3 minutes).

In another aspect, a single dose of atropine in the intranasal dry powder compositions and/or unit doses given intranasally is operable to be bioequivalent (for example, in terms of peripheral blood levels, systemic exposure of atropine) to intravenously (IV), intramuscularly (IM), or subcutaneously (SQ) injected atropine (e.g., DUODOTE® autoinjector 2.1 mg atropine). For example, in one embodiment, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%, optionally, in the fasting state.

In a further embodiment, the intranasal dry powder compositions are operable to be present in amounts of up to 100 mg, for example about: 1 to 5 mg, 5 to 10 mg, 10 to 20 mg, 20 to 40 mg, 40 to 60 mg, 60 to 80 mg, or 80 to 100 mg. In some embodiments, the compositions herein are operable to be present in about: 1, 5, 10, 15, 20, 25, 30, 35, 40, 45, or 50 mg.

Cholinesterase Reactivator Agent

In another aspect, provided herein is an intranasal dry powder composition including a cholinesterase reactivator agent. In some embodiments, the cholinesterase reactivator agent is pralidoxime chloride (monopyridinium oxime pralidoxime—2-PAM), diacetylmonoxime, monoisonitrosoacetone, obidoxime, P2S, TMB-4, or other agents with similar activity or a pharmaceutically acceptable salt thereof. In a preferred embodiment, the cholinesterase reactivator agent is pralidoxime chloride (monopyridinium oxime pralidoxime—2-PAM) or a pharmaceutically acceptable salt thereof. In some embodiments, a single dose of the cholinesterase reactivator agent is about 1 mg to about 1000 mg. In another aspect, the amount of the cholinesterase reactivator agent (e.g., pralidoxime chloride) is at least about: 1 mg, 10 mg, 100 mg, 500 mg, 600 mg, or 1000 mg in the compositions. In some embodiments, the cholinesterase reactivator agent (e.g., pralidoxime chloride) present in the compositions is about: 1 mg to 10 mg, 100 mg to 600 mg, or 600 mg to 1000 mg. In some embodiments, the cholinesterase reactivator agent herein present in the compositions is about: 1 to 5 mg, 5 to 10 mg, 10 to 20 mg, 20 to 40 mg, 40 to 60 mg, 60 to 80 mg, 80 to 100 mg, 100 to 200 mg, 200 to 500 mg, or 500 to 1000 mg. In some embodiments, the cholinesterase reactivator agent herein is at least about: 1 mg, 10 mg, 100 mg, 200 mg, 400 mg, 600 mg, 800 mg, or 1000 mg in the compositions and/or unit doses. In one instance, a single dose of the cholinesterase reactivator agent (e.g., pralidoxime chloride) is about 100 mg. In one instance, a single dose of the cholinesterase reactivator agent (e.g., pralidoxime chloride) is about 600 mg. In another related aspect, the dose of the cholinesterase reactivator agent (e.g., pralidoxime chloride) is operable to be adjusted according to the weight of the patient at an increment of at least 0.01 mg/kg, or one wherein the dose is operable to be repeated a number of times if the patient failed to improve patient symptoms. In some embodiments, the composition, in the form of a single dose, includes about 100 mg to about 600 mg of the cholinesterase reactivator agent (e.g., pralidoxime chloride).

In some embodiments, a single dose of the cholinesterase reactivator agent is about 300 mg or about 600 mg. In some embodiments, the composition, in the form of a single dose, includes about 10 mg to about 600 mg of the cholinesterase reactivator agent. In some embodiments, the composition, in the form of a single dose, includes about 600 mg or about 1000 mg of the cholinesterase reactivator agent.

A unit dosage herein is operable to range from about 1 mg to about 1000 mg. A unit dosage is also operable to be at least about: 1, 50, 100, 600, or 1000 mg of a composition. Administration of the compositions herein is operable to be repeated, e.g., every 5-20 minutes as necessary. In some embodiments, an anticholinergic agent (e.g., atropine) is operable to be used in conjunction with the cholinesterase reactivator agent (e.g., pralidoxime chloride), a composition or a unit dose including thereof, for managing patients suffering from chemical attack with nerve agents or similar type agents.

In some embodiments, the cholinesterase reactivator agent (e.g., pralidoxime chloride) is about 0.005% to about 50% w/w of the weight of the composition, for example about: 0.005%, 0.01%, 0.05%, 0.1%, 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w based on the weight of the compositions and/or unit doses. For example, the cholinesterase reactivator agent is operable to be about 2.5%, about 4%, about 7.5%, or about 15% w/w of the weight of the composition. In some embodiments, the cholinesterase reactivator agent (e.g., pralidoxime chloride) is operable to be present in an amount of at least about: 0.25% w/w, 1% w/w, 5% w/w, 10% w/w, 20% w/w, 30% w/w, 40% w/w, or 50% w/w based on the weight of the compositions and/or unit doses. In some embodiments, the cholinesterase reactivator agent (e.g., pralidoxime chloride) is operable to be present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the compositions and/or unit doses.

In one embodiment, the dry powder compositions herein are operable to increase the maximal blood concentration ($C_{max}$) of the cholinesterase reactivator agent (e.g., pralidoxime chloride) to about 7 µg/mL. In one embodiment, the compositions herein are operable to increase the blood concentration of the cholinesterase reactivator agent (e.g., pralidoxime chloride) by about 1, 2, 3, 4, 5, 6, 7, 8, 9, 10, 11, 12, 13, 14, 15, 25, or 50 µg/mL. In another embodiment, the compositions herein are operable to increase the central nervous system (CNS) concentration of the cholinesterase reactivator agent (e.g., pralidoxime chloride) by about 1, 2, 3, 4, 5, 6, 7, 8, 9, 10, 11, 12, 13, 14, 15, 25, or 50 µg/mL.

In some embodiments, the dry powder composition disclosed herein, when administered to a patient, reaches a maximal blood or CNS concentration of the cholinesterase reactivator agent (e.g., pralidoxime chloride) in less than about 60 minutes ($T_{max}$) after administration. In some embodiments, the dry powder composition, when administered to a patient, reaches a maximal blood or CNS concentration ($T_{max}$) of the cholinesterase reactivator agent (e.g., pralidoxime chloride) in less than about 60, 50, 40, 30, 20, 15, 10, 5, or 3 minutes ($T_{max}$) after administration. In one embodiment, the dry powder composition, when administered to a patient, reaches a maximal blood or CNS concentration ($T_{max}$) of the cholinesterase reactivator agent (e.g., pralidoxime chloride) in less than about 30 minutes after administration. In some embodiments, the dry powder composition, when administered to a patient, reaches a mean $AUC_{(0\text{-}180\ minutes)}$ of the cholinesterase reactivator agent (e.g., pralidoxime chloride) that is at least 20%, 30%, 40% 50%, 60%, 70%, 80%, 90%, 100%, 110%, 120%, 130%, 140%, or 150% of the mean $AUC_{(0\text{-}180\ minutes)}$ of an equivalent IV, IM, or SQ injected cholinesterase reactivator agent. In some embodiments, the dry powder composition, when administered to a patient, reaches a mean $AUC_{(0\text{-}\infty)}$ of the cholinesterase reactivator agent (e.g., pralidoxime chloride) that is at least 20%, 30%, 40% 50%, 60%, 70%, 80%, 90%, 100%, 110%, 120%, 130%, 140%, or 150% of the mean $AUC_{(0\text{-}\infty)}$ of an equivalent IV, IM, or SQ injected cholinesterase reactivator agent. In some embodiments, the equivalent IV, IM, or SQ injected cholinesterase reactivator agent (e.g., pralidoxime chloride) includes 100 mg, 200 mg, 300 mg, 400 mg, 500 mg, or 600 of the cholinesterase reactivator agent. For example, the dry powder composition, when administered to a patient, reaches a mean $AUC_{(0\text{-}180\ minutes)}$ of the cholinesterase reactivator agent that is at least 80% of the mean $AUC_{(0\text{-}180\ minutes)}$ of a 600 mg IM injected cholinesterase reactivator agent. In another instance, the dry powder composition, when administered to a patient, reaches a mean $AUC_{(0\text{-}\infty)}$ of the cholinesterase reactivator agent that is at least 80% of the mean $AUC_{(0\text{-}\infty)}$ of a 600 mg IM injected cholinesterase reactivator agent. In some embodiments, the IM injected cholinesterase reactivator agent is pralidoxime chloride injected by DUODOTE® autoinjector.

In certain embodiments, the intranasal dry powder compositions and/or unit doses herein are operable to raise the blood or CNS concentration of the cholinesterase reactivator agent (e.g., pralidoxime chloride) to about 7 µg/mL within about 3 to about 60 minutes (e.g., about: 60, 50, 40, 30, 20, 15, 10, 5, or 3 minutes) or about 10 to about 15 minutes (e.g., about: 10, 11, 12, 13, 14, or 15 minutes) of intranasal administration. In one embodiment, the compositions herein increase the blood or CNS concentration of the cholinesterase reactivator agent (e.g., pralidoxime chloride) by about 7 µg/mL (e.g., 8 or 10 µg/mL) in about 10 to about 15 minutes (e.g., about: 10, 11, 12, 13, 14, or 15 minutes) or about 3 to about 60 minutes (e.g., about: 60, 50, 40, 30, 20, 15, 10, 5, or 3 minutes).

In another aspect, a single dose of pralidoxime chloride in the intranasal dry powder compositions and/or unit doses given intranasally is bioequivalent (for example, in terms of peripheral blood levels, systemic exposure of pralidoxime) to intravenously (IV), intramuscularly (IM) or subcutaneously (SQ) injected pralidoxime chloride (e.g., DUODOTE® autoinjector 600 mg pralidoxime). For example, in one embodiment, bioequivalence means a 90% confidence interval of a mean $T_{max}$ (e.g., the time to reach maximal blood concentration), a mean $C_{max}$ (e.g., maximal blood concentration), a mean $AUC_{(0\text{-}t)}$ (e.g., area under the plasma/serum/blood concentration-time curve from time zero to time t), and/or a mean $AUC_{(0\text{-}\infty)}$ (e.g., area under the plasma/serum/blood concentration-time curve from time zero to time infinity) of the test to reference are within 80.00% to 125.00%, optionally, in the fasting state.

In a further embodiment, the intranasal dry powder compositions are present in amounts of up to 1000 mg, for example about: 10 to 100 mg, 100 to 600 mg, or 600 to 1000 mg. In some embodiments, the compositions herein are present in about: 1, 5, 10, 15, 20, 25, 30, 35, 40, 45, or 50 mg.

Vasoactive Agent

In another aspect, provided herein is an intranasal dry powder composition including a vasoactive agent. In some embodiments, the vasoactive agent is epinephrine, vasopressin, phenylephrine, a similar agent in a similar or related class, or a pharmaceutically acceptable salt thereof. In a preferred embodiment, the vasoactive agent is epinephrine or a pharmaceutically acceptable salt thereof. In some embodiments, the vasoactive agent does not include cocaine or a derivative thereof. In some embodiments, a single dose of the vasoactive agent is about 0.01 mg to about 10 mg. In another aspect, the amount of the vasoactive agent (e.g., epinephrine) is at least about: 0.01 mg, 0.05 mg, 1.0 mg, 2.0 mg, 5.0 mg, or 10 mg in the compositions. In some embodiments, the vasoactive agent (e.g., epinephrine) present in the compositions is about: 0.01 mg to 0.05 mg, 0.05 mg to 0.75 mg, 0.75 mg to 1.5 mg, 1.5 mg to 3.0 mg, 3.0 to 4.5 mg, 4.5 to 6.0 mg, 6.0 to 7.5 mg, 7.5 to 9.0 mg, or 9.0 to 10.0 mg. In some embodiments, the amount of the vasoactive agent (e.g., epinephrine) is about: 0.15, 0.3, 0.5, 0.75, 1, 1.5, 2, 3, 4, 5, 6, 7, 8, 9, or 10 mg in the compositions. In one instance, a single dose of the vasoactive agent is about 0.75 mg. In one instance, a single dose of the vasoactive agent is about 1.5 mg. In another instance, a single dose of the vasoactive agent is about 3.0 mg. In another related aspect, the dose of the vasoactive agent (e.g., epinephrine) is operable to be adjusted according to the weight of the patient at an increment of at least 0.01 mg/kg, or one wherein the dose is operable to be repeated a number of times if the patient failed to increase the patient's arterial pressure. In some embodiments, the composition, in the form of a single dose, includes about 0.01 mg to about 10 mg of the vasoactive agent. In some embodiments, the composition, in the form of a single dose, includes about 0.75 mg, 1.5 mg, or 3.0 mg of the vasoactive agent.

A unit dosage herein is operable to range from about 0.01 mg to about 1 mg, for example about: 0.1, 0.2, 0.3, 0.4, 0.5, 0.6, 0.7, 0.8, 0.9, or 1 mg of a composition. A unit dosage is also operable to be at least about: 0.01 0.1, 0.5, or 1 mg of a composition. Administration of the compositions herein are operable to be repeated, e.g., every 5-20 minutes as necessary. In some embodiments, antihistamines (e.g., $H_1$ and/or $H_2$ receptor antagonists) and/or corticosteroids are used in conjunction with the vasoactive agent (e.g., epinephrine), a composition, or a unit dose including thereof for managing patients suffering from cardiac arrest and/or hypotensive shock.

In some embodiments, the vasoactive agent is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w based on the weight of the compositions and/or unit doses. For example, the vasoactive agent is operable to be about 4%, about 7.5%, or about 15% w/w of the weight of the composition. In some embodiments, the vasoactive agent (e.g., epinephrine) is operable to be present in an amount of at least about: 0.25% w/w, 1% w/w, 5% w/w, 10% w/w, 20% w/w, 30% w/w, 40% w/w, or 50% w/w based on the weight of the compositions and/or unit doses. In some embodiments, the vasoactive agent (e.g., epinephrine) is operable to be present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the compositions and/or unit doses.

In some embodiments, the dry powder composition disclosed herein when administered to a patient, produces a maximal blood concentration ($C_{max}$) of the vasoactive agent (e.g., epinephrine) that is operable to be at least about: 2- to 3-fold, 3- to 5-fold, 5- to 7-fold, or 7- to 10-fold more than the baseline level of the vasoactive agent in the patient. In some embodiments, the dry powder composition, when administered to a patient, produces a maximal blood concentration ($C_{max}$) of the vasoactive agent at least 2-, 3-, 4-, 5-, 6-, 7-, 8-, 9-, or 10-fold more than the baseline level of the vasoactive agent in the patient. In one embodiment, the dry powder composition, when administered to a patient, produces a maximal blood concentration ($C_{max}$) of the vasoactive agent at least 2-fold more than the baseline level of the vasoactive agent in the patient. In one embodiment, the compositions herein are operable to increase the blood concentration of the vasoactive agent (e.g., epinephrine) by about 0.01 to 0.1 µg/mL. In one embodiment, the compositions herein are operable to increase the blood concentration of the vasoactive agent (e.g., epinephrine) by about 0.01, 0.02, 0.03, 0.04, 0.05, 0.06, 0.07, 0.08, 0.09, or 0.1 µg/mL.

In some embodiments, the dry powder composition disclosed herein, when administered to a patient, reaches a maximal blood concentration of the vasoactive agent (e.g., epinephrine) in less than about 60 minutes ($T_{max}$) after administration. In some embodiments, the dry powder composition, when administered to a patient, reaches a maximal blood concentration ($T_{max}$) of the vasoactive agent in less than about 60, 50, 40, 30, 20, 15, 10, 5, or 3 minutes ($T_{max}$) after administration. In one embodiment, the dry powder composition, when administered to a patient, reaches a maximal blood concentration ($T_{max}$) of the vasoactive agent in less than about 20 minutes after administration. In some embodiments, the dry powder composition, when administered to a patient, reaches a mean $AUC_{(0\text{-}180\ minutes)}$ of the vasoactive agent that is at least 20%, 30%, 40% 50%, 60%, 70%, 80%, 90%, 100%, 110%, 120%, 130%, 140%, or 150% of the mean $AUC_{(0\text{-}180\ minutes)}$ of an equivalent IV, IM, or SQ injected vasoactive agent. In some embodiments, the dry powder composition, when administered to a patient, reaches a mean $AUC_{(0\text{-}\infty)}$ of the vasoactive agent that is at least 20%, 30%, 40% 50%, 60%, 70%, 80%, 90%, 100%, 110%, 120%, 130%, 140%, or 150% of the mean $AUC_{(0\text{-}\infty)}$ of an equivalent IV, IM, or SQ injected vasoactive agent. In some embodiments, the equivalent IV, IM, or SQ injected vasoactive agent includes 0.10 mg, 0.15 mg, 0.20 mg, 0.25 mg, 0.30 mg, 0.35 mg, 0.40 mg, 0.45 mg, 0.50 mg, 0.55 mg, 0.60 mg, 0.65 mg, 0.70 mg, 0.75 mg, 0.80 mg, 0.85 mg, 0.90 mg, 0.95 mg, or 1.0 mg of the vasoactive agent. For example, the dry powder composition, when administered to a patient, reaches a mean $AUC_{(0\text{-}180\ minutes)}$ of the vasoactive agent that is at least 80% of the mean $AUC_{(0\text{-}180\ minutes)}$ of a 0.15 mg IV injected vasoactive agent. In another instance, the dry powder composition, when administered to a patient, reaches a mean $AUC_{(0\text{-}\infty)}$ of the vasoactive agent that is at least 80% of the mean $AUC_{(0\text{-}\infty)}$ of a 0.15-1 mg IV injected vasoactive agent. In some embodiments, the equivalent W, IM, or SQ injected vasoactive agent is epinephrine injected by EPIPEN® autoinjector. In some embodiments, the dry powder composition, when administered to a patient, reaches a mean $AUC_{(0\text{-}180\ minutes)}$ of the vasoactive agent that is at least 100,000 pg·min/mL, 200,000 pg·min/mL, 300,000 pg·min/mL, 400,000 pg·min/mL, 500,000 pg·min/mL, 600,000 pg·min/mL, 700,000 pg·min/mL, 800,000 pg·min/mL, 900,000 pg·min/mL, or 1,000,000 pg·min/mL. In some embodiments, the dry powder composition, when administered to a patient, reaches a mean $AUC_{(0\text{-}\infty)}$ of the vasoactive agent that is at least 100,000 pg·min/mL, 200,000 pg·min/mL, 300,000 pg·min/mL, 400,000 pg·min/mL, 500, 000 pg·min/mL, 600,000 pg·min/mL, 700,000 pg·min/mL, 800,000 pg·min/mL, 900,000 pg·min/mL, 1,000,000 pg·min/mL, 1,200,000 pg·min/mL, 1,400,000 pg·min/mL, 1,600,000 pg·min/mL, 1,800,000 pg·min/mL, or 2,000,000 pg·min/mL.

In certain embodiments, the intranasal dry powder compositions and/or unit doses herein are operable to raise the blood concentration of the vasoactive agent (e.g., epinephrine) to about 0.02 µg/mL within about 3 to about 60 minutes (e.g., about: 60, 50, 40, 30, 20, 15, 10, 5, or 3 minutes) or about 10 µg/mL within about 3 to 15 minutes (e.g., about: 3, 5, 10, 11, 12, 13, 14, or 15 minutes) of intranasal administration. In one embodiment, the compositions herein increase the blood concentration of the vasoactive agent (e.g., epinephrine) by about 0.01 to 0.04 µg/mL (e.g., 0.02 or 0.03 µg/mL) in about 10 to about 15 minutes (e.g., about: 10, 11, 12, 13, 14, or 15 minutes) or about 3 µg/mL in about 60 minutes (e.g., about: 60, 50, 40, 30, 20, 15, 10, 5, or 3 minutes).

In another aspect, a single dose of epinephrine in the intranasal dry powder compositions and/or unit doses given intranasally are bioequivalent (for example, in terms of peripheral blood levels, systemic exposure of epinephrine) to intravenously (IV), intramuscularly (IM), or subcutaneously (SQ) injected epinephrine (e.g., using EPIPEN® auto-injector of 0.3 mg for adult patients or 1 mg IV epinephrine). For example, in one embodiment, bioequivalence means a 90% confidence interval of a mean $T_{max}$ (e.g., the time to reach maximal blood concentration), a mean $C_{max}$ (e.g., maximal blood concentration), a mean $AUC_{(0-t)}$ (e.g., area under the plasma/serum/blood concentration-time curve from time zero to time t), and/or a mean $AUC_{(0-\infty)}$ (e.g., area under the plasma/serum/blood concentration-time curve from time zero to time infinity) of the test to reference are within 80.00% to 125.00%, optionally, in the fasting state.

In another aspect, the dry powder composition including epinephrine further includes a vasodilator. Advantageously, a topically acting vasodilator (e.g., phentolamine) provided at the same time in the same dose as epinephrine allows for lowering the loading dose of the epinephrine. In one embodiment, the vasodilator is an α-blocker (e.g., phentolamine). In one embodiment, the vasodilator is phentolamine or a pharmaceutically acceptable salt thereof. In some embodiments, a single dose of the vasodilator is about 0.01 mg to about 10 mg. In some embodiments, the vasodilator (e.g., phentolamine) herein is present in the compositions in about: 0.001 mg to 0.01 mg, 0.01 mg to 0.05 mg, 0.05 to 0.1 mg, 0.1 to 0.5 mg, 0.5 to 0.75 mg, 0.75 mg to 1.5 mg, 1.5 mg to 3.0 mg, 3.0 to 4.5 mg, 4.5 to 6.0 mg, 6.0 to 7.5 mg, 7.5 to 9.0 mg, or 9.0 to 10.0 mg. In some embodiments, the vasodilator (e.g., phentolamine) herein is at least about: 0.001 mg, 0.01 mg, 0.1 mg, 0.5 mg, 1.0 mg, 2.0 mg, 5.0 mg, or 10.0 mg in the compositions and/or unit doses. In some embodiments, a single dose of the vasodilator is about 0.5 mg or about 1.0 mg. In some embodiments, the composition, in the form of a single dose, includes about 0.01 mg to about 10 mg of the vasodilator. In some embodiments, the composition, in the form of a single dose, includes about 0.5 mg or about 1.0 mg of the vasodilator.

In some embodiments, the amount of the vasodilator is about 0.005% to about 50% w/w of the weight of the composition, for example about: 0.005%, 0.01%, 0.05%, 0.1%, 0.5%, 1%, 2%, 2.5%, 3%, 4%, 5%, 6%, 7%, 8%, 9%, 10%, 15%, 20%, 25%, 30%, 35%, 40%, 45%, or 50% w/w of the weight of the composition. In some embodiments, the amount of the vasodilator is about 2.5% w/w of the weight of the composition.

Anticonvulsive Agent

In one aspect, provided herein is an intranasal dry powder composition including an anticonvulsive agent. In some embodiments, the anticonvulsive agent is diazepam, lorazepam, midazolam, clonazepam, temazepam, flunitrazepam, triazolam, alprazolam, zolpidem, eszopiclone, or other agents with agonist activity at the benzodiazepine site on the GABA receptor or other agents that activate the GABA receptor or a pharmaceutically acceptable salt thereof. In a preferred embodiment, the anticonvulsive agent is diazepam or a pharmaceutically acceptable salt thereof. In some embodiments, a single dose of the anticonvulsive agent is about 0.1 mg to about 20 mg. In another aspect, the amount of the anticonvulsive agent (e.g., diazepam) is at least about: 0.1 mg, 0.5 mg, 1.0 mg, 2.0 mg, 5.0 mg, 10 mg, 15 mg, or 20 mg in the compositions. In some embodiments, the anticonvulsive agent (e.g., diazepam) present in the compositions is about: 0.1 mg to 0.5 mg, 0.5 mg to 0.75 mg, 0.75 mg to 1.5 mg, 1.5 mg to 3.0 mg, 3.0 to 4.5 mg, 4.5 to 6.0 mg, 6.0 to 7.5 mg, 7.5 to 9.0 mg, 9.0 to 10.0 mg, or 10 to 20 mg. In some embodiments, the amount of the anticonvulsive agent (e.g., diazepam) is about: 0.15, 0.3, 0.5, 0.75, 1, 1.5, 2, 3, 4, 5, 6, 7, 8, 9, 10, or 20 mg in the compositions. In one instance, a single dose of the anticonvulsive agent is about 0.75 mg. In one instance, a single dose of the anticonvulsive agent is about 1.5 mg. In another instance, a single dose of the anticonvulsive agent is about 3.0 mg. In another related aspect, the dose of the anticonvulsive agent (e.g., diazepam) is operable to be adjusted according to the weight of the patient at an increment of at least 0.01 mg/kg, or one wherein the dose is operable to be repeated a number of times if the patient failed to improve patient symptoms. In some embodiments, the composition, in the form of a single dose, includes about 0.1 mg to about 20 mg of the anticonvulsive agent. In some embodiments, the composition, in the form of a single dose, includes about 0.75 mg, 1.5 mg, 3.0 mg, or 10 mg of the anticonvulsive agent.

A unit dosage herein is operable to range from about 0.1 mg to about 20 mg, for example about: 0.1, 0.5, 1, 2, 3, 4, 5, 6, 7, 8, 9, 10, 11, 12, 13, 14, 15, 16, 17, 18, 19, or 20 mg of a composition. A unit dosage is also operable to be at least about: 0.1, 5, or 10 mg of a composition. Administration of the compositions herein are operable to be repeated, e.g., every 5-20 minutes as necessary.

In some embodiments, the anticonvulsive agent is about 0.25% to about 50% w/w of the weight of the composition, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 25%, 30%, 35%, 40%, 45%, or 50% w/w based on the weight of the compositions and/or unit doses. For example, the anticonvulsive agent is operable to be about 4%, about 7.5%, or about 15% w/w of the weight of the composition. In some embodiments, the anticonvulsive agent (e.g., diazepam) is operable to be present in an amount of at least about: 0.25% w/w, 1% w/w, 5% w/w, 10% w/w, 20% w/w, 30% w/w, 40% w/w, or 50% w/w based on the weight of the compositions and/or unit doses. In some embodiments, the anticonvulsive agent (e.g., diazepam) is operable to be present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the weight of the compositions and/or unit doses.

In one embodiment, the dry powder compositions herein are operable to increase the blood concentration of the anticonvulsive agent (e.g., diazepam) to about 0.2-2.5 µg/mL. In one embodiment, the compositions herein are operable to increase the blood concentration of the anticonvulsive agent (e.g., diazepam) by about 0.1, 0.2, 0.3, 0.4, 0.5, 0.6, 0.7, 0.8, 0.9, 1.0, 1.1, 1.2, 1.3, 1.4, 1.5, 2.0, 2.5, or 3.0 µg/mL.

In some embodiments, the dry powder composition disclosed herein, when administered to a patient, reaches a maximal blood concentration of the anticonvulsive agent (e.g., diazepam) in less than about 60 minutes ($T_{max}$) after administration. In some embodiments, the dry powder composition, when administered to a patient, reaches a maximal blood concentration ($T_{max}$) of the anticonvulsive agent in less than about 60, 50, 40, 30, 20, 15, 10, 5, or 3 minutes ($T_{max}$) after administration. In one embodiment, the dry powder composition, when administered to a patient, reaches a maximal blood concentration ($T_{max}$) of the anticonvulsive agent in less than about 30 minutes after administration. In some embodiments, the dry powder composition, when administered to a patient, reaches a mean $AUC_{(0\text{-}180\ minutes)}$ of the anticonvulsive agent that is at least 20%, 30%, 40% 50%, 60%, 70%, 80%, 90%, 100%, 110%, 120%, 130%, 140%, or 150% of the mean $AUC_{(0\text{-}180\ minutes)}$ of IM an IV, or SQ injected anticonvulsive agent. In some embodiments, the dry powder composition, when administered to a patient, reaches a mean $AUC_{(0\text{-}\infty)}$ of the anticonvulsive agent that is at least 20%, 30%, 40% 50%, 60%, 70%, 80%, 90%, 100%, 110%, 120%, 130%, 140%, or 150% of the mean $AUC_{(0\text{-}\infty)}$ of an equivalent IV, IM, or SQ injected anticonvulsive agent. In some embodiments, the IV, IM, or SQ injected anticonvulsive agent includes 1 mg, 2 mg, 2.1 mg, 3 mg, 4 mg, 5 mg, 6 mg, 7 mg, 8 mg, 9 mg, 10 mg, 15 mg, or 20 mg of the anticonvulsive agent. For example, the dry powder composition, when administered to a patient, reaches a mean $AUC_{(0\text{-}180\ minutes)}$ of the anticonvulsive agent that is at least 80% of the mean $AUC_{(0\text{-}180\ minutes)}$ of a 5 mg IV injected anticonvulsive agent. In another instance, the dry powder composition, when administered to a patient, reaches a mean $AUC_{(0\text{-}\infty)}$ of the anticonvulsive agent that is at least 80% of the mean $AUC_{(0\text{-}\infty)}$ of a 5 mg IV injected anticonvulsive agent.

In certain embodiments, the intranasal dry powder compositions and/or unit doses herein are operable to raise the blood concentration of the anticonvulsive agent (e.g., diazepam) to about 2 µg/mL within about 3 to about 60 minutes (e.g., about: 60, 50, 40, 30, 20, 15, 10, 5, or 3 minutes) or about 10 to about 15 minutes (e.g., about: 10, 11, 12, 13, 14, or 15 minutes) of intranasal administration. In one embodiment, the compositions herein increase the blood concentration of the anticonvulsive agent (e.g., diazepam) by about 2 µg/mL in about 10 to about 15 minutes (e.g., about: 10, 11, 12, 13, 14, or 15 minutes) or about 3 to about 60 minutes (e.g., about: 60, 50, 40, 30, 20, 15, 10, 5, or 3 minutes).

In another aspect, a single dose of diazepam in the intranasal dry powder compositions and/or unit doses given intranasally is bioequivalent (for example, in terms of peripheral blood levels, systemic exposure of diazepam) to intravenously (IV), intramuscularly (IM), or subcutaneously (SQ) injected diazepam. For example, in one embodiment, bioequivalence means a 90% confidence interval of a mean $T_{max}$ (e.g., the time to reach maximal blood concentration), a mean $C_{max}$ (e.g., maximal blood concentration), a mean $AUC_{(0\text{-}t)}$ (e.g., area under the plasma/serum/blood concentration-time curve from time zero to time t), and/or a mean $AUC_{(0\text{-}\infty)}$ (e.g., area under the plasma/serum/blood concentration-time curve from time zero to time infinity) of the test to reference are within 80.00% to 125.00%, optionally, in the fasting state.

Enabling Agents

In one embodiment, the intranasal dry powder compositions and/or unit doses include at least one enabling agent. The at least one enabling agent includes, but is not limited to, at least one catechol-o-methyl transferase (COMT) inhibitor, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

Additional details regarding nasal delivery of drugs, including information regarding enabling agents, are disclosed in (1) Bourganis V, Kammona O, Alexopoulos A, Kiparissides C. Recent advances in carrier mediated nose-to-brain delivery of pharmaceutics. Eur J Pharm Biopharm. 2018 July; 128:337-362. doi: 10.1016/j.ejpb.2018.05.009. Epub 2018 May 4. PMID: 29733950; (2) Davis S S, Illum L. Absorption enhancers for nasal drug delivery. Clin Pharmacokinet. 2003; 42(13):1107-28. doi: 10.2165/00003088-200342130-00003. PMID: 14531723; (3) Ganger S, Schindowski K. Tailoring Compositions for Intranasal Nose-to-Brain Delivery: A Review on Architecture, Physico-Chemical Characteristics and Mucociliary Clearance of the Nasal Olfactory Mucosa. Pharmaceutics. 2018 Aug. 3; 10(3):116. doi: 10.3390/pharmaceutics10030116. PMID: 30081536; PMCID: PMC6161189; and (4) Tiozzo Fasiolo L, Manniello M D, Tratta E, Buttini F, Rossi A, Sonvico F, Bortolotti F, Russo P, Colombo G. Opportunity and challenges of nasal powders: Drug composition and delivery. Eur J Pharm Sci. 2018 Feb. 15; 113:2-17. doi: 10.1016/j.ejps.2017.09.027. Epub 2017 Sep. 20. PMID: 28942007, each of which is incorporated herein by reference in its entirety.

In one embodiment, the intranasal dry powder compositions and/or unit doses include at least one COMT inhibitor. In some embodiments, the COMT inhibitor is a reversible COMT inhibitor. In one embodiment, the COMT inhibitor is entacapone or a pharmaceutically acceptable salt thereof. In some embodiments, a single dose of the COMT inhibitor is about 5 mg to about 800 mg. In one embodiment, a single dose of the COMT inhibitor is about 5 mg to about 200 mg. In some embodiments, the COMT inhibitor herein is present in the compositions in about: 0.05 mg to 0.1 mg, 0.1 mg to 0.5 mg, 0.5 mg to 0.75 mg, 0.75 mg to 1.5 mg, 1.5 mg to 3.0 mg, 3.0 mg to 4.5 mg, 4.5 mg to 6.0 mg, 6.0 mg to 7.5 mg, 7.5 mg to 9.0 mg, 9.0 mg to 10.0 mg, 10 mg to 25 mg, 25 mg to 50 mg, 50 mg to 100 mg, 100 mg to 150 mg, 150 mg to 200 mg, or 200 mg to 400 mg. In some embodiments, the COMT inhibitor herein is at least about: 0.001 mg, 0.01 mg, 0.1 mg, 0.5 mg, 1.0 mg, 2.0 mg, 5.0 mg, or 10.0 mg in the compositions and/or unit doses. In some embodiments, a single dose of the COMT inhibitor is about 0.5 mg, about 1.0 mg, about 5.0 mg, about 10.0 mg, about 25 mg, about 50 mg, about 75 mg, about 100 mg, about 150 mg, or about 200 mg. In some embodiments, the composition, in the form of a single dose, includes about 0.01 mg to about 25 mg of the COMT inhibitor. In some embodiments, the composition, in the form of a single dose, includes about 0.5 mg, about 1.0 mg, about 5.0 mg, about 10.0 mg, about 25 mg, about 50 mg, about 75 mg, about 100 mg, about 150 mg, or about 200 mg of the COMT inhibitor.

In one embodiment, the intranasal dry powder compositions and/or unit doses include at least one epinephrine potentiator. In one embodiment, the at least one epinephrine potentiator includes, but is not limited to, histidine, a flavonoid, a local anesthetic (e.g., benzocaine, lidocaine), a COMT inhibitor, levothyroxine sodium, at least one antihistamine, at least one tricyclic antidepressant, and/or a monoamine oxidase inhibitor (MAO) inhibitor. In one embodiment, the at least one tricyclic antidepressant includes amitriptyline, amoxapine, desipramine, doxepin, imipramine, nortriptyline, protriptyline, and/or trimipramine.

In one embodiment, the intranasal dry powder compositions and/or unit doses include at least one atropine potentiator. In one embodiment, the at least one atropine potentiator includes, but is not limited to, amantadine, at least one antihistamine, at least one tricyclic antidepressant, quinidine, and/or disopyramide. In one embodiment, the at least one tricyclic antidepressant includes amitriptyline, amoxapine, desipramine, doxepin, imipramine, nortriptyline, protriptyline, and/or trimipramine.

In one embodiment, the intranasal dry powder compositions and/or unit doses include at least one mucoadhesive. In one embodiment, the at least one mucoadhesive includes a starch, crystalline cellulose, a cellulose derivative, a polymer (e.g., chitosan, a carbopol (e.g., carbopol 943), carbophil, carbomer), a polyacrylic acid or polyacrylic acid derivative, a protein (e.g., mucin, lactoferrin, transferrin), and/or lecithin. See, e.g., (1) Takeuchi H, Thongborisute J, Matsui Y, Sugihara H, Yamamoto H, Kawashima Y. Novel mucoadhesion tests for polymers and polymer-coated particles to design optimal mucoadhesive drug delivery systems. Adv Drug Deliv Rev. 2005 Nov. 3; 57(11):1583-94. doi: 10.1016/j.addr.2005.07.008. Epub 2005 Sep. 16. PMID: 16169120; (2) D Tabor, Surface forces and surface interactions, J. Colloid Interface Sci., Volume 58, Issue 1, 1977, Pages 2-13, https://doi.org/10.1016/0021-9797(77)90366-6; and (3) Robert J Good, Surface free energy of solids and liquids: Thermodynamics, molecular forces, and structure, J. Colloid Interface Sci., Volume 59, Issue 3, 1977, Pages 398-419, https://doi.org/10.1016/0021-9797(77)90034-0.

In one embodiment, the intranasal dry powder compositions and/or unit doses include at least one absorption enhancer. In one embodiment, the at least one absorption enhancer includes a flavonoid (e.g., Vitamin P-like compound), vasopressin, methylphenidate, tropolone, desmethyl papaverine, pyrogallol, an amino acid (e.g., histidine), an antihistamine, an amphetamine, a local anesthetic, norepinephrine, isoproterenol, hydrocortisone, tripelennamine, bufotenine, harmine, methergine, a ganglionic blocker, guanethidine, mescaline, cocaine, lysergic acid diethylamide (LSD), or an enantiomer, diastereoisomer, racemate, prodrug, or salt of such compounds.

In one embodiment, the intranasal dry powder compositions and/or unit doses include at least one permeability enhancer and/or at least one mucosal permeation enhancer. In one embodiment, the at least one permeability enhancer and/or at least one mucosal permeation enhancer increases a fraction of the at least one active pharmaceutical ingredient that reaches circulation by at least about 10%, at least about 25%, preferably at least 50%, and most preferably at least 100%. In one embodiment, the at least one permeability enhancer includes a bile salt, alkyl glycoside, a polymer, a tight junction modulation peptide, a lipid, a surfactant, a cyclodextrin, a chelator (e.g., EDTA), a Hsieh enhancer, a cyclic lactone, a cyclic diester, a cyclic ketone, a fatty acid, a salicylate, and/or an amphiphilic steroid (e.g., a fusidic acid derivative). Tight junction modulating peptides are described in U.S. Patent Publication No. 20090220435, which is incorporated herein by reference in its entirety. In one embodiment, the cyclodextrin includes alpha-cyclodextrin, beta-cyclodextrin, gamma-cyclodextrin, hydroxypropyl-beta-cyclodextrin, and/or sulfobutylether beta-cyclodextrin. In one embodiment, the lipid includes 1,2-Dioleoyl-sn-Glycero-3 Ethylphosphocholine, 1,2-di-O-phytanoyl-glycero-3-phosphocholine, 1-O-hexadecyl-2-acetoyl-sn-glycerol, 1-O-octadecyl-2-O-methyl-glycerol-3-phosphocholine, 16:0-09:0(ALDO)PC, 16:0-09:0(COOH) PC, 3-beta-hydroxy-5alpha-cholest-8(14)-en-15-one, C10 sucrose, C12 maltose, C12 sucrose, C14 maltose, C16-09:0, C6 glucose, C6 maltose, C7 glucose, C8 glucose, Cardiolipin (sodium salt), Ceramide (brain porcine), Ceramide C10:0, Ceramide C12:0, Ceramide C14:0, Ceramide C16:0, Ceramide C17:0, Ceramide C18:0, Ceramide C18:1, Ceramide C20:0, Ceramide C24:0, Ceramide C24:1, Ceramide C2:0, Ceramide C4:0, Ceramide C6:0, Ceramide C8:0, Cerebroside (brain porcine), Cerebroside Sulfatide (porcine), Dimethyl sphingosine, Egg Ceramide, Galactosyl sphingosine, Glucosyl-sphingosine, Lactosyl(B) Sphingosine, Lyso-PAF, N-acetoyl ceramide-1-phosphate, N-octanoyl ceramide-1-phosphate, PGPC1, POVPC, Phosphatidylinositol (Soy), Phosphatidylinositol (bovine), Platelet-Activation Factor, Porcine brain ganglioside, Sphingomyelin (brain porcine), Sphingosine-1-phosphate, and trimethylsphingosine. The lipid is preferably a glycosylated sphingosine, an alkylglucoside, an oxidized lipid, and/or an ether lipid (PAF). In one embodiment, the fatty acid is sodium caprate, sodium laurate, sodium caprylate, capric acid, lauric acid, caprylic acid, and/or an acyl carnitine (e.g., palmitoyl carnitine, stearoyl carnitine, myristoyl carnitine, lauroyl carnitine). In one embodiment, the salicylate is sodium salicylate, 5-methoxy salicylate, and methyl salicylate. Hsieh enhancers are described in U.S. Pat. Nos. 5,023,252 and 5,731,303, each of which is incorporated herein by reference in its entirety. Cyclic lactones, cyclic diesters, and cyclic ketones are described in U.S. Pat. No. 8,481,043, which is incorporated herein by reference in its entirety. Amphiphilic steroids are discussed in U.S. Pat. Nos. 4,548,922 and 4,746,508, each of which is incorporated herein by reference in its entirety. In one preferred embodiment, the at least one permeability enhancer and/or the at least one mucosal permeation enhancer is a generally accepted as safe (GRAS) pharmaceutical excipient. Alternatively, the at least one permeability enhancer and/or the at least one mucosal permeation enhancer is a near-GRAS excipient and/or a non-GRAS excipient. In one embodiment, the at least one permeation enhancer and/or the at least one mucosal permeation enhancer is about 1% to about 30% w/w of the weight of the composition.

In one embodiment, the intranasal dry powder compositions and/or unit doses include at least one surfactant. The at least one surfactant is a non-ionic surfactant, an ionic surfactant, a cationic surfactant, an anionic surfactant, and/or a zwitterionic surfactant. Examples of the at least one surfactant compatible with the present invention include, but are not limited to, sodium glycocholate, sodium taurocholate, polyoxyethylene lauryl ether, polyacrylic acid gel, sodium lauryl sulfate, polysorbate, and/or sodium deoxycholate.

In a preferred embodiment, the intranasal dry powder compositions and/or unit doses do not include a surfactant. Some liquid compositions of drugs require a surfactant to prevent aggregation of the active ingredient. Advantageously, dry powder compositions do not require a surfactant.

In one embodiment, the intranasal dry powder compositions and/or unit doses include at least one surface modifier. In one embodiment, the at least one surface modifier includes a lubricant (e.g., magnesium stearate), a fluidizing agent (e.g., talc, silicon dioxide), a nitric oxide (NO) stimulator, chitosan, and/or a chitosan derivative.

In one embodiment, the intranasal dry powder compositions and/or unit doses include at least one sustained release agent. In one embodiment, the at least one sustained release agent is achieved by manipulating one or more of the at least one active pharmaceutical ingredient to control its dissolution and/or the composition in which the at least one active pharmaceutical ingredient is suspended. In one embodiment, excipients with mucoadhesive and/or viscosity enhancing characteristics are incorporated. Additionally or alternatively, the composition is operable to reversibly diminish mucocilliary clearance.

In one embodiment, the intranasal dry powder compositions and/or unit doses include at least one anticaking agent. The at least one anticaking agent includes, but is not limited to, tribasic calcium phosphate. In one embodiment, the at least one anticaking agent is about 0.5% to about 5% w/w of the weight of the composition. In some embodiments, the at least one anticaking agent has an average particle diameter of about 100 µm or less, for example about: 90 to 100 µm, 80 to 90 µm, 70 to 80 µm, 60 to 70 µm, 50 to 60 µm, 40 to 50 µm, 30 to 40 µm, 20 to 30 µm, or 10 to 20 µm. In some embodiments, the at least one anticaking agent has an average particle diameter of about 30 µm to 100 µm.

In one embodiment, the intranasal dry powder compositions and/or unit doses include at least one systemic vasodilator and/or at least one nasal mucosal vasodilator. In one embodiment, the at least one systemic vasodilator and/or the at least one nasal mucosal vasodilator includes an angiotensin-converting enzyme (ACE) inhibitor (e.g., Benazepril (Lotensin), Captopril (Capoten), Enalopril (Vasotec), Fosinopril (Monopril), Lisinopril (Prinivil, Zestril), Minoxidil (Loniten), Meoexipril (Univasc), Perindopril (Aceon), Quinapril (Accupril), Ramipril (Altace), Trandolaptril (Mavik)), an angiotensin II receptor antagonist (e.g., Losartan, Candesatran, Valsartan, Irbesartan, Telmisartan, Eprosartan, Olmesartan, Azilsartan), phentolamine, nitroglycerine, hydralazine, isosorbide mononitrate, isosorbide dinitrate, papaverine hydrochloride or mesylate, cocaine, ethyl nitrate, diltiazem, urapidil, nicorandil, sodium nitroprusside, glyceryl trinitrate-verapamil, phenoxybenzamine, dopexamine, chloropromazine, propiverine hydrochloride, or an enantiomer, diastereoisomer, racemate, prodrug, or salt of such compounds. In a preferred embodiment, the at least one systemic vasodilator and/or the at least one nasal mucosal vasodilator is phentolamine.

In one embodiment, the intranasal dry powder compositions and/or unit doses include at least one agent that reduces mucosal transit time. In one embodiment, the at least one agent that reduces mucosal transit time includes a polyacrylate mucoadhesive agent and/or a peptide. See, e.g., WIPO Publication No. WO2003037355, which is incorporated herein by reference in its entirety.

In one embodiment, the intranasal dry powder compositions and/or unit doses include at least one agent that increases mucosal absorption or adhesion or transport. In one embodiment, the at least one agent that increases mucosal absorption or adhesion or transport includes a surfactant, gelling microsphere, chitosan, sodium lauryl sulfate, sodium salicylate, oleic acid, lecithin, dehydrated alcohol, Tween, polyoxyl 40 stearate, polyoxyl ethylene 40 stearate, propylene glycol, hydroxyl fatty acid ester of polyethylene glycol, glycerol monooleate, fusieates, a bile salt, octoxynol, polysorbate 20, polysorbate 80, DDPC, DPPC, a chelator (e.g., EDTA, EGTA, citrate), and/or a surfactant. See, e.g., (1) Ilium L and Fisher A N (1997) Intranasal delivery of peptides and proteins, in Inhalation Delivery of Therapeutic Peptides and Proteins (Adjei A L and Gupta P K eds), Marcel Dekker, New York and (2) Costantino H R, Illum L, Brandt G, Johnson P H, Quay S C. Intranasal delivery: physicochemical and therapeutic aspects. Int J Pharm. 2007 Jun. 7; 337(1-2):1-24. doi: 10.1016/j.ijpharm.2007.03.025. Epub 2007 Mar. 25. PMID: 17475423, each of which is incorporated herein by reference in its entirety.

In one embodiment, the intranasal dry powder compositions and/or unit doses include at least one chelator. In one embodiment, the at least one chelator includes ethylenediaminetetraacetic acid (EDTA), ethylene glycol-bis(βaminoethyl ether)-N,N,N',N'-tetraacetic acid (EGTA), and/or citrate.

In one embodiment, the intranasal dry powder compositions and/or unit doses include at least one steroid. In one embodiment, the at least one steroid includes at least one corticosteroid. In one embodiment, the at least one steroid is hydrocortisone, beclomethasone, fluticasone, triamcinolone, flunisolide, mometasone, ciclesonide, and/or budesonide.

In one embodiment, the intranasal dry powder compositions and/or unit doses include at least one non-sulfite stabilizer. In one embodiment, the at least one non-sulfite stabilizer is ascorbic acid.

In one embodiment, the intranasal dry powder compositions and/or unit doses include at least one preservative. The at least one preservative includes, but is not limited to a paraben, benzalkonium chloride, phenyl ethyl alcohol, ethylenediaminetetraacetic acid (EDTA), benzoyl alcohol, a thiol, glutathione, glutathione reductase, glutathione peroxidase, hydroquinone, amikasin sulfate, apomorphine hydrochloride, metaraminol, levobunonol, levobunonol hydrochloride, acamprosate calcium, fenoldopam, hydrocortisone/neomycin sulfate/polymyxin B, dexamethasone sodium phosphate, hydromorphone, dobutamine, epinephrine, etidicaine/epinephrine bitartrate, gentamycin, tinzaparin, isoproternerol, ketoconazole, sodium sulfacetamide, norepinephrine, bupivacaine/epinephrine bitartrate, morphine, tobramycin, rotigotine, orphenadrine, procaine, nalbuphine, oxytetracycline, nortriptyline, perphenazine, promethazine hydrochloride, prednisolone acetate, propofol, mesalamine, trimethoprim/sulfamethoxazole, carisoprodol/aspirin/codeine, streptomycin, mafenide acetate, tetracycline hydrochloride, pentazocine lactate, chlorpromazine, triethylperazine maleate, fluorinolone acetonide/hydroquinone/tretinoin, acetaminophen/codeine, doxycline calcium, and/or lidocaine/epinephrine. In one embodiment, the at least one preservative is about 0.01% to about 5% w/w of the weight of the composition, for example about: 0.01%, 0.05%, 0.1%, 0.2%, 0.5%, 1%, 2%, 3%, 4%, or 5% w/w based on the weight of the compositions and/or unit doses. In one embodiment, the at least one preservative is about 0.01% to 5%, 0.02% to 4%, or 0.05% to 2.5% w/w based on the weight of the compositions and/or unit doses. In a preferred embodiment, the at least one preservative is sulfite-free.

In a preferred embodiment, the intranasal dry powder compositions and/or unit doses do not include a preservative. Preservatives (e.g., sodium bisulfite, which is present in EpiPen® and other autoinjectors) can cause an allergic reaction in some individuals. Because aqueous compositions of drugs are often sensitive to light and heat, they generally include a preservative to improve stability. The intranasal dry powder compositions and/or unit doses of the present invention advantageously do not require a preservative. Additionally, not including a preservative in the intranasal dry powder compositions and/or unit doses reduces the risk of further allergic reaction(s) and/or sensitivities. "Despite documentation of sensitivity, sulfites should not be withheld from patients experiencing a life-threatening emergency. Non-sulfited alternatives are often available, and should be used preferentially." See, e.g., Roth J V, Shields A. A dilemma: How does one treat anaphylaxis in the sulfite allergic patient since epinephrine contains sodium metabisulfite? Anesth Analg. 2004 May; 98(5):1499; author reply 1500. doi: 10.1213/01.ane.0000120092.39021.f2. PMID: 15105239, which is incorporated herein by reference in its entirety. Also see, e.g., Susan C. Smolinske (1992) Review of Parenteral Sulfite Reactions, Journal of Toxicology: Clinical Toxicology, 30:4, 597-606, DOI: 10.3109/15563659209017945, which is incorporated herein by reference in its entirety. Drugs without sulfites are often available in a medical setting (e.g., hospital, clinic) because environmental conditions can be controlled. Aqueous preparations and auto-injectors generally contain preservatives because they are intended for ambient use. There is a long-standing, unmet need for dry powder compositions that do not contain a preservative.

In one embodiment, the intranasal dry powder compositions and/or unit doses include at least one thickening agent. In one embodiment, the at least one thickening agent includes microcrystalline cellulose and/or carboxymethylcellulose sodium.

In one embodiment, the intranasal dry powder compositions and/or unit doses include at least one humectant. The at least one humectant includes, but is not limited to, glycerine, glycerol, sorbitol, mannitol, and/or vegetable oil.

In one embodiment, the intranasal dry powder compositions and/or unit doses include at least one antihistamine. In one embodiment, the at least one antihistamine includes an $H_1$ receptor antagonist and/or an $H_2$ receptor antagonist. In one embodiment, the $H_1$ receptor antagonist includes an ethylenediamine, an ethanolamine, an alkylamine, a piperazine, a tricyclic, and/or a tetracyclic. In one embodiment, the at least one antihistamine includes loratadine, desloratadine, diphenhydramine, doxylamine, fexofenadine, chlorpheniramine, hydroxyzine, cetirizine, levocetrizine, brompheniramine, clemastine, carbinoxamine, azelastine, emadastine, mepyramine, promethazine, cyproheptadine, doxepin, mirtazapine, cimetidine, famotidine, nizatidine, roxatidine, lafutidine, and/or levocabastine. Additional information regarding antihistamines are disclosed in U.S. Patent Publication No. 20100055152 and U.S. Pat. No. 8,263,581, each of which is incorporated herein by reference in its entirety.

In one embodiment, the intranasal dry powder compositions and/or unit doses include at least one solubilizing agent. The at least one solubilizing agent includes, but is not limited to, a glycol, an alcohol, 2-(2-ethoxyethoxy)ethanol, a cyclodextrin, and/or a glyceride (e.g., a medium chain glyceride, LABRASOL®).

In one embodiment, the intranasal dry powder compositions and/or unit doses include at least one masking agent (e.g., taste, smell). In a preferred embodiment, the at least one masking agent includes, but is not limited to, at least one sweetener and/or at least one flavoring agent. The at least one sweetener includes, but is not limited to, saccharin (e.g., sodium salt, calcium salt), fructose, dextrose, aspartame, acesulfame potassium, glycerin, sucralose, maltodextrin, sucrose, glucose, maltose, xylitol, sorbitol, erythritol, and/or mannitol. In one embodiment, the at least one masking agent includes phenethyl alcohol, vanilla, cherry, cinnamon, lavender, lemon, menthol, orange, peppermint, spearmint, raspberry, strawberry, grape, ethyl vanillin, coriander, ginger, nutmeg, cardamom, butterscotch, cocoa, acacia syrup, anethole, anise oil, benzaldehyde, ethyl acetate, methyl salicylate, and/or tolu. In one embodiment, the at least one masking agent is about 0.001% to about 1% w/w of the weight of the composition, for example about: 0.001%, 0.005%, 0.01%, 0.02%, 0.05%, 0.1%, 0.2%, 0.3%, 0.4%, 0.5%, 0.6%, 0.7%, 0.8%, 0.9%, or 1% w/w based on the weight of the compositions and/or unit doses. In one embodiment, the at least one masking agent is about 0.01% to 0.5%, 0.02% to 0.2%, or 0.015% to 0.15% w/w based on the weight of the compositions and/or unit doses.

In one embodiment, the intranasal dry powder compositions and/or unit doses include at least one antioxidant. The at least one antioxidant includes, but is not limited to, sodium metabisulfite, sodium bisulfate, butylated hydroxytoluene, tocopherol, ascorbic acid (Vitamin C), glutathione, glutathione reductase, glutathione peroxidase, superoxide dismutase (CuZn—SOD), superoxide reductase, carnosine, ergothionene, ovothiol, lipoic acid, thioctic acid, thioredoxin peroxidase, and/or recombinant thermostable variants thereof. In one embodiment, the at least one antioxidant is about 0.0001% to about 10% w/w of the weight of the composition, for example about: 0.0001%, 0.0005%, 0.001%, 0.005%, 0.01%, 0.02%, 0.05%, 0.1%, 0.5%, 1%, 2%, 3%, 4%, 5%, 6%, 7%, 8%, 9%, or 10% w/w based on the weight of the compositions and/or unit doses. In one embodiment, the at least one antioxidant is about 0.001% to 5%, 0.05% to 2%, or 0.1% to 1% w/w based on the weight of the compositions and/or unit doses.

In one embodiment, the intranasal dry powder compositions and/or unit doses include at least one viscosity enhancing agent. The at least one viscosity enhancing agent includes, but is not limited to, a cellulose derivative (e.g., crystalline cellulose, amorphous cellulose, methylcellulose, carboxymethylcellulose, ethylcellulose, hypromellose, hydroxylpropyle cellulose, or a salt thereof), carrageenan, guar gum, an alginate, a carbomer, a polyethylene glycol, propylene glycol, a polyvinyl alcohol, xanthan gum, a polyvinylpyrrolidone (PVP), chitosan, a polysaccharide, a starch, and/or carbopol. In one embodiment, the at least one viscosity enhancing agent is about 0.1% to about 10% w/w of the weight of the composition, for example about: 0.1%, 0.5%, 1%, 2%, 3%, 4%, 5%, 6%, 7%, 7.5%, 8%, 9%, or 10% w/w based on the weight of the compositions and/or unit doses.

In one embodiment, the intranasal dry powder compositions and/or unit doses include at least one dispersing agent. In one embodiment, the at least one dispersing agent includes citric acid.

In one embodiment, the intranasal dry powder compositions and/or unit doses include at least one colorant. In a preferred embodiment, the at least one colorant is non-allergenic.

In one embodiment, the intranasal dry powder compositions and/or unit doses include at least one buffering agent. The at least one buffering agent includes, but is not limited to, a phosphate, a citrate, a succinate, histidine, glycine, arginine, malic acid, tartaric acid, acetic acid, benzoic acid, lactic acid, ascorbic acid, ammonium chloride, sodium chloride, potassium chloride, zinc chloride, calcium chloride, sodium acetate trihydrate, and/or triethanolamine. In one embodiment, the at least one buffering agent is about 0.10% to about 3% w/w of the weight of the composition, for example about: 0.01%, 0.05%, 0.1%, 0.2%, 0.3%, 0.4%, 0.5%, 0.6%, 0.7%, 0.8%, 0.9%, 1%, 1.5%, 2%, 2.5%, or 3% w/w based on the weight of the compositions and/or unit doses. In one embodiment, the at least one buffering agent is about 0.05% to 2.5% w/w based on the weight of the compositions and/or unit doses.

In one embodiment, the compositions of the present invention do not include a pH buffer. For example, the most stable pH for many drugs is below 7. A pH buffer (e.g., hydrochloric acid) is often to liquid compositions to reduce the pH. However, a low pH (e.g., between 2.5 and 5) may cause some discomfort for patients. Advantageously, the compositions of the present invention do not require a pH buffer.

Carriers and Excipients

In some embodiments, the dry powder composition further includes at least one carrier and/or excipient (e.g., at least one pharmaceutically acceptable carrier and/or excipient). In one embodiment, the at least one carrier and/or excipient includes, but is not limited to, lactose (e.g., D-lactose, lactose monohydrate), sucrose, glucose, dextrose, trehalose, sodium carboxymethylcellulose (CMC), mannitol, sorbitol, malitol, xylitol, maltose, cellulose and derivatives, starch and derivatives, microcrystalline cellulose, hypromellose acetate succinate (HPMCAS), a cyclodextrin (e.g., dimethyl-beta-cyclodextrin), calcium carbonate, citric acid, tartaric acid, glycine, leucine, polyvinyl pyrrolidone (PVP), a polyethylene glycol, polysorbate (e.g., Polysorbate 80 (e.g., TWEEN® 80)), chitosan, hyaluronic acid (e.g., sodium hyaluronate), sodium carboxymethyl cellulose (NaCMC), magnesium stearate, calcium stearate, an alkyl saccharide (e.g., n-Dodecyl β-D-Maltoside (DDM)), niacin, ethanol (e.g., dried ethanol), caffeine, benzalkonium chloride, ubiquinone (i.e., coenzyme Q10), magnesium oxide, sodium chloride, dodecylphosphocholine (DPC), silicone, gelatin, a polyacrylic acid polymer (e.g., CARBOPOL® 934), sodium taurocholate, carnitine hydrochloride, Poloxamer 188, histidine, arginine, crospovidone, ethylenediaminetetraacetic acid (EDTA), sodium starch glycolate, and/or a mixture of mannitol and hydroxypropyl methylcellulose (HPMC). In one embodiment, the at least one carrier and/or excipient includes at least one carbohydrate. In one embodiment, the at least one carbohydrate includes at least one monosaccharide, at least one disaccharide, at least one cyclodextrin, at least one polysaccharide, at least one starch, and/or at least one cellulose. In one embodiment, the at least one carrier and/or excipient includes at least one salt. The at least one salt includes, but is not limited to, sodium chloride, potassium chloride, sodium phosphate, calcium phosphate, calcium sulfate, and/or magnesium sulfate.

In some embodiments, the at least one carrier and/or excipient includes a first cellulose and/or a second cellulose. In some embodiments, the first cellulose is a crystalline cellulose. In some embodiments, the first cellulose is a microcrystalline cellulose. In some embodiments, the first cellulose has an average particle diameter of about 100 μm or less, for example about: 90 to 100 μm, 80 to 90 μm, 70 to 80 μm, 60 to 70 μm, 50 to 60 μm, 40 to 50 μm, 30 to 40 μm, 20 to 30 μm, or 10 to 20 μm. In some embodiments, the first cellulose has an average particle diameter of less than about 100 μm, 90 μm, 80 μm, 70 μm, 60 μm, 50 μm, 40 μm, 30 μm, 20 μm, 10 μm, or 5 μm. In some embodiments, the first cellulose has an average particle diameter of about 30 μm or less. In some embodiments, the at least one carrier and/or excipient includes a second cellulose. In some embodiments, the second cellulose is a crystalline cellulose. In some embodiments, the second cellulose is a microcrystalline cellulose. In some embodiments, the at least one carrier and/or excipient further includes a starch. In some embodiments, the at least one carrier and/or excipient includes a second cellulose and starch. In some embodiments, the second cellulose and/or starch have an average particle diameter of about 30 to about 100 μm, for example about: 30-40 μm, 30-50 μm, 30-60 μm, 30-70 μm, 30-80 μm, or 30-90 μm. In some embodiments, the second cellulose and/or starch have an average particle diameter of less than about 100 μm, 90 μm, 80 μm, 70 μm, 60 μm, 50 μm, 40 μm, 30 μm, 20 μm, 10 μm, or 5 μm. In some embodiments, the second cellulose, the starch, or the second cellulose and starch each individually has an average particle diameter of about 30 to about 100 μm.

In one embodiment, the at least one carrier and/or excipient present in the intranasal dry powder compositions is a mixture of a first microcrystalline cellulose, a second microcrystalline cellulose, a starch, and/or tribasic calcium phosphate. In one embodiment, the at least one carrier and/or excipient includes: i) a first crystalline cellulose with an average particle diameter of about 30 μm or less, for example about: 30-10 μm, 30-15 μm, 30-20 μm, or 30-25 μm; ii) tribasic calcium phosphate; and iii) a second crystalline cellulose, or starch, with an average particle diameter of about 30 to about 100 μm, for example about: 30-40 μm, 30-50 μm, 30-60 μm, 30-70 μm, 30-80 μm, or 30-90 μm. See, e.g., U.S. Pat. No. 8,337,817, which is incorporated herein by reference in its entirety.

In one embodiment, the at least one carrier and/or excipient includes particles having an average diameter of 1 μm to 100 μm. This is applicable to unimodal or multimodal compositions. In a preferred embodiment, the at least one carrier and/or excipient includes particles having an average diameter of at least 15 μm. Advantageously, an average diameter greater than 15 μm prevents particles from entering the lungs. In a preferred embodiment, the at least one carrier and/or excipient includes particles having an average diameter of about 50 μm. In one embodiment, the at least one carrier and/or excipient includes particles having an average diameter of about 25 μm to about 75 μm.

In one embodiment, an average particle diameter of a dry powder composition is determined using a laser-diffraction particle size distribution analyzer. In some embodiments, an average particle diameter of a dry powder composition is determined using sieve sorting.

The compositions of the present invention preferably do not include any liquid carriers (e.g., water, alcohol, and/or propylene glycol). Liquid carriers often require additional preservatives to improve stability. Advantageously, dry powder compositions do not require a preservative, which reduces the risk for allergic reactions.

Particle Characteristics

The at least one active pharmaceutical ingredient, the at least one enabling agent, and/or the at least one carrier are operable to be individually substantially amorphous or crystalline. In some embodiments, the compositions and/or unit doses provided herein are in the form of particles, and the shapes of the particles are operable to be individually, e.g., cylindrical, discoidal, spherical, tabular, ellipsoidal, angular, and/or irregular.

In some embodiments, the average particle diameter of the at least one active pharmaceutical ingredient, the at least one enabling agent, and/or the at least one carrier and/or excipient are, individually, up to 100 µm, up to 50 µm, or up to 30 µm. In a preferred embodiment, the average particle diameter of the at least one active pharmaceutical ingredient, the at least one enabling agent, and/or the at least one carrier and/or excipient are, individually, less than or equal to 50 µm. In one embodiment, the average particle diameter of the at least one active pharmaceutical ingredient, the at least one enabling agent, and/or the at least one carrier and/or excipient are, individually, about: 10-20, 20-30, 30-40, 40-50, 50-60, 60-70, 70-80, 80-90, or 90-100 µm. In another embodiment, the average particle diameter of the at least one active pharmaceutical ingredient, the at least one enabling agent, and/or the at least one carrier and/or excipient are, individually, about: 10, 15, 20, 25, 30, 35, 40, 45, 50, 55, 60, 65, 70, 75, 80, 85, 90, 95, or 100 µm.

In some embodiments, the median particle diameter of the at least one active pharmaceutical ingredient herein is about 30 µm (e.g., 28.7 µm). In some embodiments, the median particle diameter of the at least one active pharmaceutical ingredient herein is about: 10-50, 20-40, or 25-35 µm. In one embodiment, 90% of particles of the at least one active pharmaceutical ingredient herein have a particle diameter under about 50 µm (e.g., about 45.5 µm). In another embodiment, 90% of particles of the at least one active pharmaceutical ingredient herein have a particle diameter under about: 40, 45, 35, 30, 25, or 20 µm. In yet another embodiment, about 10% of particles of the at least one active pharmaceutical ingredient herein have a particle diameter under about 20 µm (e.g., about 17.3 µm). In still another embodiment, about 10% of particles of the at least one active pharmaceutical ingredient herein have a particle diameter under about: 19, 18, 17, 16, 15, 14, 13, 12, 11, or 10 µm.

In a preferred embodiment, the average particle size, and/or the mean particle size is greater than 15 µm. Advantageously, an average particle size and/or a mean particle size greater than 15 µm avoids any entry of the particles into the lungs. In a preferred embodiment, the average particle size and/or the mean particle size is about 50 µm. In one embodiment, the average particle size and/or the mean particle size is between about 25 µm and about 75 µm.

In one aspect, the compositions or unit doses herein are not or do not include spray-dried particles. In some embodiments, the compositions herein do not possess a fine particle fraction of less than 5.6 microns of at least about 45 percent. In some embodiments, the compositions herein do not include particles including: (a) about 11 to about 21 weight percent atropine; (b) about 62 to about 82 weight percent leucine; and/or (c) about 7 to about 17 weight percent sodium tartrate.

Referring now to the drawings in general, the illustrations are for the purpose of describing one or more preferred embodiments of the invention and are not intended to limit the invention thereto.

Delivery Devices and Packaging

In one embodiment, provided herein is therapeutic product including: (a) a dose of an intranasal dry powder compositions disclosed herein; (b) a dry powder nasal delivery device; and/or (c) a secondary packaging for the device that provides protection against humidity, light, or oxygen or other gases that are operable to reduce the stability or physical characteristics of the dry powder compositions disclosed herein. An example of such a delivery device is the UDS-P nasal delivery device manufactured by Aptar Pharma.

Nasal devices are disclosed in U.S. Pat. Nos. 10,814,079; 10,806,870; 10,668,228; 9,808,818; 9,156,048; 8,734,392; 8,016,209; 7,988,073; 7,950,391; 7,946,455; 7,878,352; 7,389,946; 7,387,265; 7,353,971; 7,216,781; 7,100,601; 7,073,731; 7,011,234; 6,877,672; 6,725,857; 6,708,846; 6,679,248; 6,626,379; 6,554,203; 6,484,715; 6,461,322; 6,450,216; 6,427,680; 6,425,499; 6,398,074; 6,367,473; 6,264,065; 6,261,274; 6,234,366; 6,209,760; 6,179,164; 6,029,663; 5,901,883; 5,568,884; 5,328,099; and 5,240,149, U.S. Publication Nos. 2019358417, 2016318051, 2015299846, 2014103064, 2014034663, 2014000588, 2013312740, 2013171334, 2013171330, 2013149459, 2013081953, 2013022750, 2012318677, 2011233232, 2011194110, 2010078447, 2007272764, 2004084554, and 2002079326, and U.S. application Ser. No. 16/814,997, each of which is incorporated herein by reference in its entirety.

In one embodiment, the delivery device includes at least one nasal probe that is operable to be replaced between discharges, so that the device is operable to be used to treat two or more individuals. The packaging of the delivery device includes with a plurality of replaceable nasal probes (e.g., corresponding to a number of doses in the device). In contrast to the existing injectors, wherein the needle comes in contact with tissue and blood of each individual, this embodiment of the delivery device advantageously enables the more rapid treatment of a plurality of patients. Additionally, this embodiment of the delivery device and the set of replaceable nasal probes reduces the physical space required for carriage or storage of the quantity of pharmaceutical agent needed to respond to a plurality of patients (e.g., on a battlefield, occupants of a train car, in an ambulance, etc.).

In one embodiment, the delivery device includes a reservoir that holds the dry powder composition. The delivery device preferably includes a reservoir and means for expelling a pharmaceutical dose in the form of a spray. In one embodiment, the reservoir includes one dose. Alternatively, the reservoir is operable to contain a plurality of pharmaceutical doses (e.g., at least 4 doses, at least 8 doses, at least 20 doses, at least 50 doses, etc.). In one embodiment, the reservoir has a fill weight of at least 10 mg. In another embodiment, the reservoir has a fill weight of between about 10 mg and about 80 mg (e.g., about 10 mg, 20 mg, 30 mg, 40 mg, 50 mg, 60 mg, 70 mg, or 80 mg). In one embodiment, the reservoir has a fill volume of at least 50 mm$^3$. In another embodiment, the reservoir has a fill volume of between about 50 mm$^3$ and about 300 mm$^3$ (e.g., about 50 mm$^3$, 80 mm$^3$, 100 mm$^3$, 130 mm$^3$, 150 mm$^3$, 175 mm$^3$, 200 mm$^3$, 225 mm$^3$, 250 mm$^3$, 275 mm$^3$, or 300 mm$^3$). In one embodiment, the delivery device includes a plurality of individual reservoirs, each containing a pharmaceutical dose (e.g., blisters). In some embodiments, the delivery device is disposable. In some embodiments, the delivery device is reusable. In some embodiments, the delivery device is recyclable. In some embodiments, the package further includes one intranasal delivery device.

In some embodiments, the device is operable to be programmed to dispense one or more pharmaceutical doses. In one embodiment, the nasal device is designed for discharge of multiple spray doses, e.g., 1, 2, 3, 4, 5, 6, 7, 8, 9, 10, or more. In one embodiment, the nasal device is designed to administer the intended dose with multiple sprays, e.g., two sprays, one in each nostril or in one nostril, or as a single spray, or to vary the dose in accordance with the body weight or maturity of the patient.

In one aspect, the dry powder composition is operable to be a multi-unit package. In some embodiments, the package includes multiple reservoirs, wherein each reservoir contains a single dose of the dry powder composition. In some embodiments, the package includes one apparatus and multiple reservoirs, wherein each reservoir contains a single dose of the dry powder composition. In some embodiments, the package includes multiple apparatuses, wherein each apparatus contains one reservoir, which contains a single dose of the dry powder composition. In an embodiment, the apparatus includes a pump spray device in which the means for expelling a single or multiple doses includes a metering pump or a sterile single dose disposable device. In one embodiment, the dose to be delivered is operable to be metered by the spray pump. In one embodiment, the spray pump is operable to be finger or hand actuated. The apparatus herein is operable to be a single-use device or a multiple-use device. In one embodiment, the single-use device is operable to be preloaded with a drug composition and disposed of after use. In one embodiment, the multiple-use device is operable to accept encapsulated compositions with negligible residue build-up even after high usage.

In one aspect, the multi-unit package herein allows for easy and quick visual verification of units used. In some embodiments, the package is labeled for easy and quick visual verification of units used. In some embodiments, the package is color labeled for easy and quick visual verification of units used. In some embodiments, the package is labeled for easy and quick visual verification of the number of units which have been removed and used, and by extension the amount of drug that has been delivered to the patient.

In a preferred embodiment, the delivery device does not require priming or shaking. The delivery device is preferably operable to dispense a dose from any position (i.e., 360° functionality).

FIG. 1 illustrates one embodiment of a nasal delivery device according to the present invention. The nasal delivery device 100 includes a plurality of components. In a preferred embodiment, the plurality of components includes a ball 102, a center piece 104, a container or reservoir 106, an actuator 108, a bottom 110, and a piston 112. In one embodiment, the plurality of components is formed of at least one plastic. The at least one plastic includes, but is not limited to, polypropylene (e.g., high density polypropylene (HDPE), linear low-density polyethylene (LLDPE)) and/or polyethylene. In one embodiment, one or more of the plurality of components further includes a dye or a colorant. The piston 112 is operable to push upward into the center piece 104. The center piece 104 comes into contact with the ball 102. Movement pushes the piston 112, the center piece 104, and the ball 102 upwards, which dispenses the dry powder composition from a tip or nasal probe of the delivery device 100.

Figure 2:
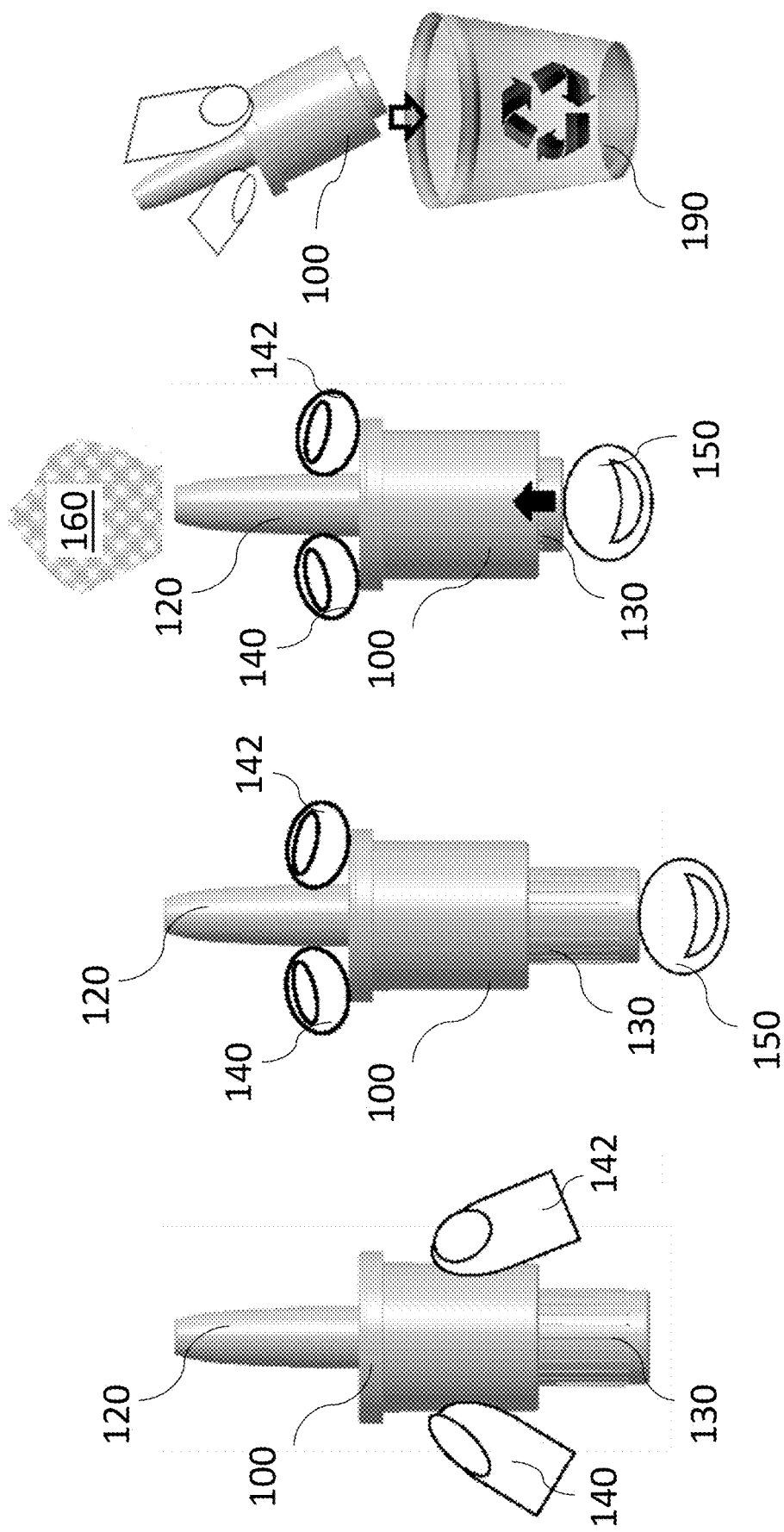
FIG. 2A illustrates a nasal delivery device at rest according to one embodiment of the present invention.
FIG. 2B illustrates positioning of fingers and a thumb on the nasal delivery device according to one embodiment of the present invention.
FIG. 2C illustrates discharge of the nasal delivery device according to one embodiment of the present invention.
FIG. 2D illustrates disposal of the nasal delivery device following use according to one embodiment of the present invention.

FIGS. 2A-2D illustrate one embodiment of a method of using a nasal delivery device according to the present invention. FIG. 2A illustrates one embodiment of the nasal delivery device 100 at rest. The nasal delivery device 100 includes a nasal probe 120 and a push button 130. FIG. 2B illustrates positioning of a first finger 140 and a second finger 142 on the nasal delivery device 100 according to one embodiment of the present invention. A thumb 150 is positioned on the push button 130 of the nasal delivery device 100. To discharge the nasal delivery device 100, the thumb 150 presses up on the push button 130 of the nasal delivery device 100 as shown in FIG. 2C. Discharge causes particles 160 to be expelled from the nasal delivery device 100 (e.g., into a nasal passage). The nasal delivery device 100 is preferably operable to be disposed of (e.g., in a recycling can 190) following use as shown in FIG. 2D.

Figure 3:
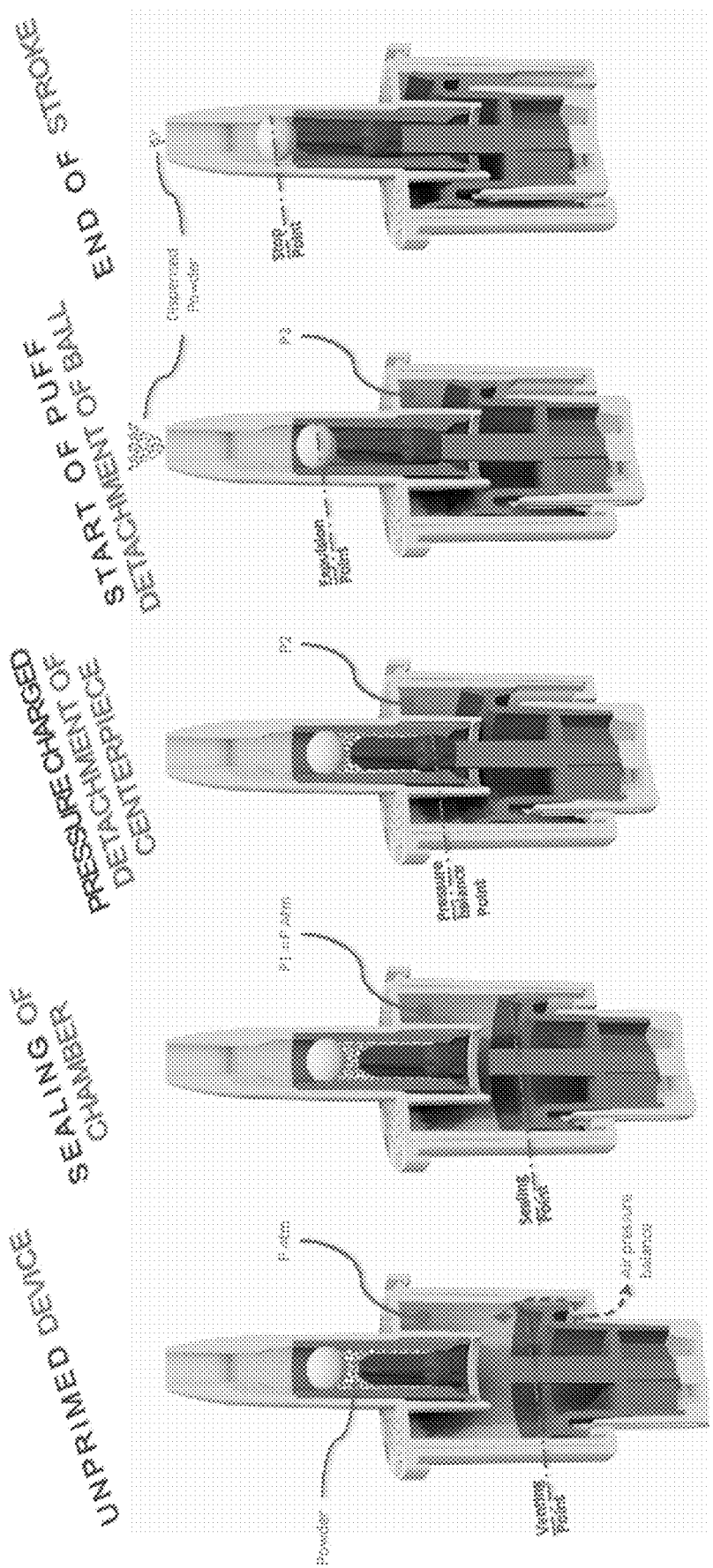
FIG. 3 illustrates the nasal delivery device in an unprimed state, with a sealed chamber, pressure charged detachment of a centerpiece, a start of a discharge, and an end of a stroke according to one embodiment of the present invention.

FIG. 3 illustrates the nasal delivery device in an unprimed state, with a sealed chamber, pressure charged detachment of a centerpiece, a start of a discharge, and an end of a stroke according to one embodiment of the present invention.

In one embodiment, the delivery device includes a counter or indicator. In one embodiment, the counter or the indicator is mechanical. Alternatively, the counter or indicator is electronic. In one embodiment, the electronic counter or indicator includes a sensor that is adapted to detect a displacement or a deformation of a portion of the delivery device (e.g., when the dry powder composition is dispensed). In one embodiment, the electronic counter or indicator includes a display (e.g., LCD screen), a power supply (e.g., battery, rechargeable battery), a timer, a clock, at least one processor, at least one memory, a communication interface, and/or a printed circuit board (PCB). The sensor preferably transmits a signal to the PCB that causes the display to change when the delivery device is actuated. The at least one memory is operable to store information generated by the delivery device and/or the sensor. In one embodiment, the communications interface is operable to transmit data wirelessly (e.g., via BLUETOOTH®). In one embodiment, the data is transmitted wirelessly to at least one remote device (e.g., smartphone, tablet, etc.). The at least one remote device preferably includes a mobile application with a graphical user interface (GUI). In one embodiment, the mobile application tracks an expiration date of a delivery device, tracks use of the delivery device (e.g., remaining doses), and/or prompts ordering of another delivery device after use of the delivery device. In one embodiment, the at least one remote device is operable to provide messaging and/or notifications between a user and a third party (e.g., healthcare provider, parent, caregiver, emergency services, pharmacy). For example, the at least one remote device provides a notification to the third party when the delivery device dispenses a dose and/or provides a notification on a screen of the at least one remote device. In one embodiment, the notification includes instructions and/or a video for how to use the delivery device. In one embodiment, the delivery device displays a time of dose dispensation on the display (e.g., from the timer or the clock). Advantageously, this alerts the third party to the emergency situation (e.g., allergic reaction, anaphylaxis, cardiac arrest, poisoning, seizure) and/or use of the device (e.g., to order a new delivery device). In the case of an emergency situation, conveying to the third party the time of dose dispensation is significant, as in many medical events a second dose is required. Thus, the knowledge of how much time has passed since the initial dosing is operable to guide the decision of whether to administer subsequent doses. In one embodiment, the at least one remote device is operable to transmit the data to at least one remote server. In another embodiment, the delivery device further includes an accelerometer and/or a gyroscope to detect movement of the delivery device. In one embodiment, the remote device is operable to transmit location data (e.g., to the third party) after the delivery device is discharged. In one embodiment, the location data is obtained from the remote device. Additionally or alternatively, the device further includes a global positioning system (GPS) device or is coupled to a GPS device operable to provide location data. Advantageously, this alerts the third party to the emergency situation (e.g., allergic reaction, anaphylaxis, cardiac arrest, poisoning, seizure). In one example, a third party (e.g., emergency services, a parent, and/or a healthcare provider) is alerted when the delivery device is discharged. In a preferred embodiment, the location of the delivery device is provided to the third party. Wireless communication in delivery devices is disclosed in U.S. Pat. Nos. 10,967,140; 7,861,943; and 6,886,556 and U.S. Patent Publication Nos. 20200164164, 20200246562, 20200155775, and 20190134322, each of which is incorporated herein by reference in its entirety.

The delivery device is preferably packaged in at least one secondary packaging. The at least one secondary packaging is operable to protect the delivery device from external elements (e.g., light, humidity, oxygen or other gases). The at least one secondary package includes, but is not limited to, a vial, a tube, a container, a bottle, a box, and/or a carton. In one embodiment, the at least one secondary package includes a desiccant or other agents that assist with stability of the composition (e.g., by preventing effects of temperature, light, humidity, oxygen or other gases). In one embodiment, the desiccant is included as a liner (e.g., a tube liner). In one embodiment, the at least one secondary package is formed of a plastic. In one embodiment, the plastic is a desiccant plastic. In one embodiment, the desiccant plastic includes a base polymer, a channeling agent, and a desiccant. Such materials are described in, for example U.S. Pat. Nos. 5,911,937; 6,080,350; 6,124,006; 6,130,263; 6,174,952; 6,194,079; 6,214,255; 6,221,446; 6,486,231; 7,005,459; and 9,902,788, each of which is incorporated herein by reference in its entirety. Advantageously, the desiccant removes moisture within the packaging and improves the stability of the API in the delivery device.

In one embodiment, the delivery device and/or one or more of the at least one secondary packaging includes a tamper resistant seal. In one embodiment, the one or more of the at least one secondary packaging and/or the delivery device includes a sensor to detect if the tamper resistant seal is removed. For example, the one or more of the at least one secondary packaging and/or the delivery device includes a smart sticker with a sensor that sends an alert (e.g., to a remote device) when a signal within the sensor is broken. In one embodiment, a notification that the sensor detected the removal of the tamper resistant seal is transmitted to the mobile application and/or a third party. Advantageously, this provides notification that the delivery device is exposed to external elements (e.g., humidity). Additionally or alternatively, one or more of the at least one secondary packaging is child resistant.

In one embodiment, one or more of the at least one secondary packaging includes an authentication method to ensure that the delivery device enclosed in the at least one secondary packaging is from the manufacturer (e.g., and not counterfeit). In one embodiment, the authentication method includes, but is not limited to, at least one code (e.g., serial number, bar code), at least one image, at least one text, and/or at least one tracker (e.g., RFID chip). In one embodiment, the at least one authentication method is verifiable via the mobile application.

Figure 4:
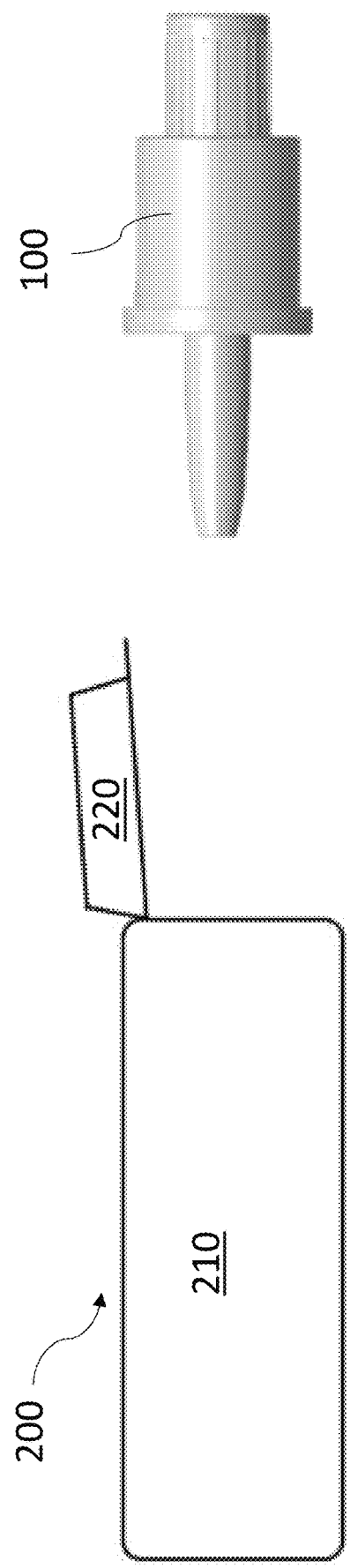
FIG. 4 illustrates a delivery device and a secondary packaging in the form of a container according to one embodiment of the present invention.

FIG. 4 illustrates one embodiment of a delivery device 100 and a secondary packaging in the form of a container 200. The delivery device 100 is operable to be stored in the container 200. The container 200 includes a base 210 and a lid 220. In one embodiment, the lid 220 is connected and/or attached to the base 210. Alternatively, the lid 220 is not connected and/or attached to the base 210 (e.g., screw on lid). Examples of a container compatible with the present invention include, but are not limited to, those disclosed in U.S. Pat. Nos. 9,834,341; 10,472,136; and 10,974,887, each of which is incorporated herein by reference in its entirety.

Figure 5:
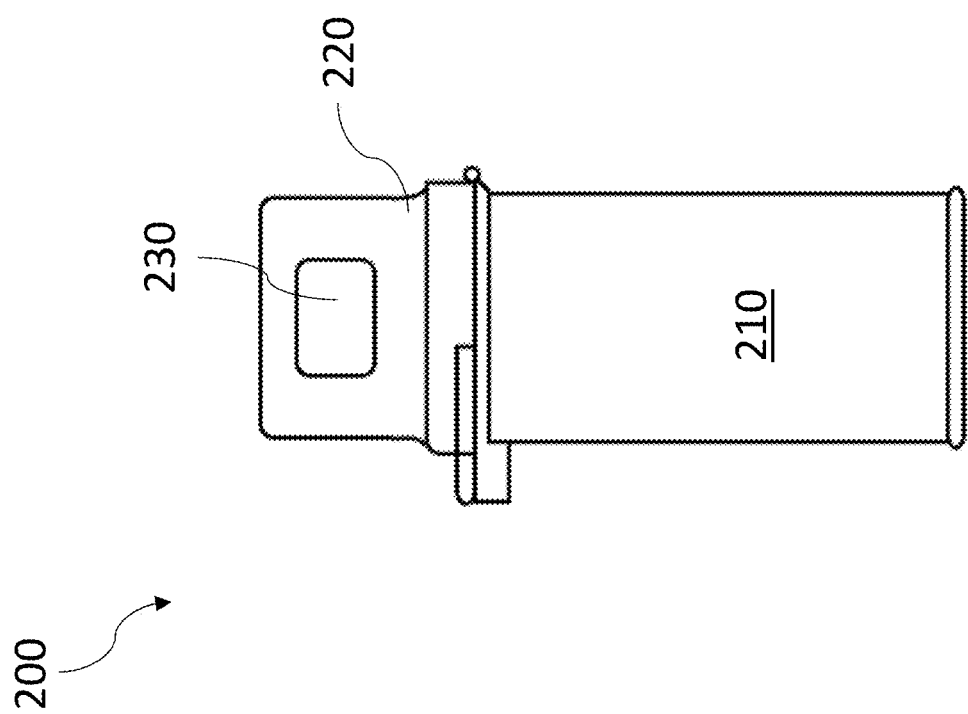
FIG. 5 illustrates a secondary packaging in the form of a container according to one embodiment of the present invention.

FIG. 5 illustrates one embodiment of a secondary packaging in the form of a container 200. The container 200 includes a base 210 and a lid 220. The container 200 is operable to store the delivery device (not shown). The lid 220 further includes a hole 230. The hole 230 is operable to attach the container 200 to a ring. The ring is further operable to attach the container 200 to a keychain or a set of keys, a backpack, a purse, or other personal item. Advantageously, this helps to ensure that the delivery device is conveniently located at all times.

In one embodiment, the at least one secondary package (e.g., carton) includes a first delivery device and a second delivery device. When providing medications, the lowest effective dose is desired. If a patient does not adequately respond to delivery of a first dose from the first delivery device, the second delivery device is operable to provide a second dose. Advantageously, this also ensures that a second dose is available if the first delivery device is not used properly. However, unlike auto-injectors, the nasal delivery device is not subject to a syringe misfiring.

The nasal delivery device preferably meets regulatory conditions described in Guidance for Industry, FDA, July 2002: Nasal Spray and Inhalation Solution, Suspension and Spray Drug Products: Chemistry, Manufacturing, and Controls Documentation; EMEA—Guideline on the Pharmaceutical Quality of Inhalation and Nasal Products (2006); Guidance for Industry, FDA, July 2002: Nasal Spray and Inhalation Solution, Suspension and Spray Drug Products: Drug Product Characterization Study; ISO 11608-1:2014 Needle-based injection systems for medical use—Requirements and test methods; ISO 20072:2009 Aerosol drug delivery device design verification—Requirements and test methods; ASTM D999-08(2015), Standard Test Methods for Vibration Testing of Shipping Containers, ASTM International, West Conshohocken, Pa., 2015; ASTM D4169-16, Standard Practice for Performance Testing of Shipping Containers and Systems, ASTM International, West Conshohocken, Pa., 2016; and/or EMEA—ICH Topic Q 1 A (R2) Stability Testing of new Drug Substances and Products (2003), each of which is incorporated herein by reference in its entirety.

In a further aspect, the compositions herein are also operable to be administered using a nasal metered dose spray, a metered dose inhaler, or a measured dose inhaler.

Additional information about the nasal delivery device is included in U.S. Provisional Patent Application No. 63/290,948, which is incorporated herein by reference in its entirety.

Training Device

In one embodiment, the present invention includes a training device. Advantageously, the training device educates a patient on proper use of the nasal delivery device, providing the patient with a greater level of confidence in the event of an emergency when the delivery device must be used. Patients with auto-injectors routinely receive training with a training device. such as in a prescribing physician office or at a dispensing pharmacy. This creates familiarity with the device operation and is intended to reduce errors in usage and hesitancy to use the device in an emergency.

Delay in administering medications is associated with increased morbidity. However, many patients fear needles despite the training for auto-injectors. There is a long-standing, unmet need for a training device for medication delivery that provides confidence in device operation while not invoking a fear of needles.

Example Combinations

The following are examples of embodiments used in combination. However, the present disclosure is not limited to the example embodiments provided below. The intranasal dry powder compositions and/or unit doses are operable to include any combination of the at least one active pharmaceutical ingredient, the at least one enabling agent, and/or the at least one carrier and/or excipient.

Example 1

In one embodiment, the intranasal dry powder compositions and/or unit doses include an anticholinergic agent (e.g., atropine) and a cholinesterase reactivator agent (e.g., pralidoxime chloride). In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 2

In one embodiment, the intranasal dry powder compositions and/or unit doses include a vasoactive agent (e.g., epinephrine). In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 3

In one embodiment, the intranasal dry powder compositions and/or unit doses include a vasoactive agent (e.g., epinephrine) and at least one antihistamine. In one embodiment, the at least one antihistamine includes, but is not limited to, diphenhydramine, doxylamine, loratadine, desloratadine, cetirizine, levocetirizine, fexofenadine, famotidine, cimetidine, and/or nizatidine. In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 4

In one embodiment, the intranasal dry powder compositions and/or unit doses include a vasoactive agent (e.g., epinephrine) and at least one steroid (e.g., hydrocortisone). In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 5

In one embodiment, the intranasal dry powder compositions and/or unit doses include a vasoactive agent (e.g., epinephrine) and a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 6

In one embodiment, the intranasal dry powder compositions and/or unit doses include an anticonvulsive agent (e.g., diazepam). In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 7

In one embodiment, the intranasal dry powder compositions and/or unit doses include a vasoactive agent (e.g., epinephrine) and an anticonvulsive agent (e.g., diazepam). In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 8

In one embodiment, the intranasal dry powder compositions and/or unit doses include a vasoactive agent (e.g., epinephrine), an anticonvulsive agent (e.g., diazepam), and at least one antihistamine. In one embodiment, the at least one antihistamine includes, but is not limited to, diphenhydramine, doxylamine, loratadine, desloratadine, cetirizine, levocetirizine, fexofenadine, famotidine, cimetidine, and/or nizatidine. In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 9

In one embodiment, the intranasal dry powder compositions and/or unit doses include a vasoactive agent (e.g., epinephrine), an anticonvulsive agent (e.g., diazepam), and at least one steroid (e.g., hydrocortisone). In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 10

In one embodiment, the intranasal dry powder compositions and/or unit doses include an anticholinergic agent (e.g., atropine), a cholinesterase reactivator agent (e.g., pralidoxime chloride), and a vasoactive agent (e.g., epinephrine). In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 11

In one embodiment, the intranasal dry powder compositions and/or unit doses include an anticholinergic agent (e.g., atropine), a cholinesterase reactivator agent (e.g., pralidoxime chloride), a vasoactive agent (e.g., epinephrine), and at least one antihistamine. In one embodiment, the at least one antihistamine includes, but is not limited to, diphenhydramine, doxylamine, loratadine, desloratadine, cetirizine, levocetirizine, fexofenadine, famotidine, cimetidine, and/or nizatidine. In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine.

In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 12

In one embodiment, the intranasal dry powder compositions and/or unit doses include an anticholinergic agent (e.g., atropine), a cholinesterase reactivator agent (e.g., pralidoxime chloride), a vasoactive agent (e.g., epinephrine), and at least one steroid (e.g., hydrocortisone). In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 13

In one embodiment, the intranasal dry powder compositions and/or unit doses include an anticholinergic agent (e.g., atropine), a cholinesterase reactivator agent (e.g., pralidoxime chloride), a vasoactive agent (e.g., epinephrine), and a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 14

In one embodiment, the intranasal dry powder compositions and/or unit doses include an anticholinergic agent (e.g., atropine), a cholinesterase reactivator agent (e.g., pralidoxime chloride), a vasoactive agent (e.g., epinephrine), a vasodilator (e.g., phentolamine), and at least one antihistamine. In one embodiment, the at least one antihistamine includes, but is not limited to, diphenhydramine, doxylamine, loratadine, desloratadine, cetirizine, levocetirizine, fexofenadine, famotidine, cimetidine, and/or nizatidine. In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 15

In one embodiment, the intranasal dry powder compositions and/or unit doses include an anticholinergic agent (e.g., atropine), a cholinesterase reactivator agent (e.g., pralidoxime chloride), a vasoactive agent (e.g., epinephrine), a vasodilator (e.g., phentolamine), and at least one steroid (e.g., hydrocortisone). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 16

In one embodiment, the intranasal dry powder compositions and/or unit doses include an anticholinergic agent (e.g., atropine), a cholinesterase reactivator agent (e.g., pralidoxime chloride), and an anticonvulsive agent (e.g., diazepam). In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 17

In one embodiment, the intranasal dry powder compositions and/or unit doses include an anticholinergic agent (e.g., atropine), a cholinesterase reactivator agent (e.g., pralidoxime chloride), an anticonvulsive agent (e.g., diazepam), and a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 18

In one embodiment, the intranasal dry powder compositions and/or unit doses include an anticholinergic agent (e.g., atropine), a cholinesterase reactivator agent (e.g., pralidoxime chloride), a vasoactive agent (e.g., epinephrine), and an anticonvulsive agent (e.g., diazepam). In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 19

In one embodiment, the intranasal dry powder compositions and/or unit doses include an anticholinergic agent (e.g., atropine), a cholinesterase reactivator agent (e.g., pralidoxime chloride), a vasoactive agent (e.g., epinephrine), an anticonvulsive agent (e.g., diazepam), and at least one antihistamine. In one embodiment, the at least one antihistamine includes, but is not limited to, diphenhydramine, doxylamine, loratadine, desloratadine, cetirizine, levocetirizine, fexofenadine, famotidine, cimetidine, and/or nizatidine. In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 20

In one embodiment, the intranasal dry powder compositions and/or unit doses include an anticholinergic agent (e.g., atropine), a cholinesterase reactivator agent (e.g., pralidoxime chloride), a vasoactive agent (e.g., epinephrine), an anticonvulsive agent (e.g., diazepam), and at least one steroid (e.g., hydrocortisone). In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 21

In one embodiment, the intranasal dry powder compositions and/or unit doses include an anticholinergic agent (e.g., atropine), a cholinesterase reactivator agent (e.g., pralidoxime chloride), a vasoactive agent (e.g., epinephrine), an anticonvulsive agent (e.g., diazepam), and a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 22

In one embodiment, the intranasal dry powder compositions and/or unit doses include an anticholinergic agent (e.g., atropine), a cholinesterase reactivator agent (e.g., pralidoxime chloride), a vasoactive agent (e.g., epinephrine), an anticonvulsive agent (e.g., diazepam), a vasodilator (e.g., phentolamine), and at least one antihistamine. In one embodiment, the at least one antihistamine includes, but is not limited to, diphenhydramine, doxylamine, loratadine, desloratadine, cetirizine, levocetirizine, fexofenadine, famotidine, cimetidine, and/or nizatidine. In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 23

In one embodiment, the intranasal dry powder compositions and/or unit doses include an anticholinergic agent (e.g., atropine), a cholinesterase reactivator agent (e.g., pralidoxime chloride), a vasoactive agent (e.g., epinephrine), an anticonvulsive agent (e.g., diazepam), a vasodilator (e.g., phentolamine), and at least one steroid (e.g., hydrocortisone). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 24

In one embodiment, the intranasal dry powder compositions and/or unit doses include an anticholinergic agent (e.g., atropine), a cholinesterase reactivator agent (e.g., pralidoxime chloride), a vasoactive agent (e.g., epinephrine), an anticonvulsive agent (e.g., diazepam), a vasodilator (e.g., phentolamine), and a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 25

In one embodiment, the intranasal dry powder compositions and/or unit doses include an anticholinergic agent (e.g., atropine), a cholinesterase reactivator agent (e.g., pralidoxime chloride), a vasoactive agent (e.g., epinephrine), an anticonvulsive agent (e.g., diazepam), a vasodilator (e.g., phentolamine), a COMT inhibitor (e.g., entacapone), and at least one antihistamine. In one embodiment, the at least one antihistamine includes, but is not limited to, diphenhydramine, doxylamine, loratadine, desloratadine, cetirizine, levocetirizine, fexofenadine, famotidine, cimetidine, and/or nizatidine. In one embodiment, the intranasal dry powder compositions and/or unit doses further include at least one enabling agent and/or at least one carrier and/or excipient.

The at least one enabling agent includes, but is not limited to, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Example 26

In one embodiment, the intranasal dry powder compositions and/or unit doses include an anticholinergic agent (e.g., atropine), a cholinesterase reactivator agent (e.g., pralidoxime chloride), a vasoactive agent (e.g., epinephrine), an anticonvulsive agent (e.g., diazepam), a vasodilator (e.g., phentolamine), a COMT inhibitor (e.g., entacapone), and at least one steroid (e.g., hydrocortisone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and polysorbate.

Kits

As previously described, in one embodiment, the present invention includes at least one kit. In one embodiment, the kit includes: (a) a dose of an intranasal dry powder composition disclosed herein and (b) instructions reciting when the dry powder composition in (a) is to be administered to a subject. In some embodiments, the kit further includes at least one intranasal delivery apparatus for dispensing the dry powder composition. In some embodiments, each of the at least one intranasal delivery apparatus is operable to deliver a therapeutically acceptable amount of the dry powder composition. In some embodiments, the apparatus is operable to intranasally deliver a therapeutically acceptable amount of the dry powder composition. In a preferred embodiment, the dry powder composition is delivered intranasally.

In another preferred embodiment, the kit includes a plurality of nasal devices. For example, and not limitation, the plurality of nasal devices includes a first nasal device, a second nasal delivery device, a third nasal delivery device, and/or a fourth nasal delivery device. In one embodiment, the plurality of nasal devices includes at least two nasal delivery devices including the same dry powder composition. For example, and not limitation, the plurality of nasal devices includes a dry powder composition including an anticholinergic agent (e.g., atropine) and a cholinesterase reactivator agent (e.g., pralidoxime chloride). In one embodiment, the plurality of nasal devices includes three nasal devices including a dry powder composition including an anticholinergic agent (e.g., atropine) and a cholinesterase reactivator agent (e.g., pralidoxime chloride).

In one embodiment, the plurality of nasal devices includes a first nasal device having a first dry powder composition and a second nasal device having a second dry powder composition. For example, and not limitation, the first nasal device includes a first dry powder composition including an anticholinergic agent (e.g., atropine) and a cholinesterase reactivator agent (e.g., pralidoxime chloride), and the second nasal device includes a second dry powder composition including a vasoactive agent (e.g., epinephrine), an anticonvulsive agent (e.g., diazepam), a vasodilator (e.g., phentolamine), a COMT inhibitor (e.g., entacapone), at least one antihistamine, and/or at least one steroid (e.g., hydrocortisone).

In one embodiment, the plurality of nasal devices includes a first nasal device having a first dry powder composition, a second nasal device having a second dry powder composition, and/or a third nasal device having a third dry powder composition. For example, and not limitation, the first nasal device includes a first dry powder composition including an anticholinergic agent (e.g., atropine) and a cholinesterase reactivator agent (e.g., pralidoxime chloride); the second nasal device includes a second dry powder composition including a vasoactive agent (e.g., epinephrine), a vasodilator (e.g., phentolamine), a COMT inhibitor (e.g., entacapone), at least one antihistamine, and/or at least one steroid (e.g., hydrocortisone); and the third nasal device includes a third dry powder composition including an anticonvulsive agent (e.g., diazepam), a COMT inhibitor (e.g., entacapone), at least one antihistamine, and/or at least one steroid (e.g., hydrocortisone).

In one embodiment, the kit is included in a pouch. In one embodiment, the pouch includes at least one closeable opening. In one embodiment, the at least one closeable opening is operable to open and/or close via at least one securing mechanism. The at least one securing mechanism includes, but is not limited to, at least one zipper, a hook and loop system (e.g., VELCRO®), at least one button, at least one snap, at least one hook, at least one tie, at least one clip, and/or at least one buckle. The pouch is preferable waterproof or water resistant.

In another embodiment, the kit is included in a hard case. In one embodiment, the hard case is formed of polypropylene or acrylonitrile butadiene styrene (ABS). The hard case is preferably waterproof or water resistant. In one embodiment, the hard case includes at least one handle (e.g., for carrying the hard case) and/or at least one loop. In one embodiment, the at least one handle and/or at least one loop is operable to attach a carabiner or other hook.

In one embodiment, the pouch and/or the hard case is MOLLE-compatible. In one embodiment, the pouch incorporates a pouch attachment ladder system (PALS), which is a grid of webbing used to attach smaller equipment onto load-bearing platforms, such as vests and backpacks. For example, the PALS grid consists of horizontal rows of 1-inch (2.5 cm) webbing, spaced about one inch apart, and reattached to the backing at 1.5-inch (3.8 cm) intervals. In one embodiment, the webbing is formed of nylon (e.g., cordura nylon webbing, MIL-W-43668 Type III nylon webbing).

In one embodiment, an exterior finish of the pouch and/or the hard case is operable to be any color including, but not limited to, white, brown, green, orange (e.g., international orange), yellow, black, red, or blue, or any pattern (e.g., camouflage). In one embodiment, the exterior of the pouch and/or the hard case includes a reflective tape, fabric, or material. Advantageously, the reflective tape, fabric, or material improves visibility of the user in low-light conditions.

Methods of Treatment

Provided herein are methods of treating a patient by intranasally administering the dry powder composition disclosed herein. Also provided herein are methods of treating a patient by using the delivery devices and/or kits disclosed herein.

In one embodiment, the patient has been exposed to at least one organophosphate compound. The at least one organophosphate compound includes, but is not limited to, sarin (GB), tabun (GA), soman (GD), cyclosarin (GF), VX, VR (Russian VX), diisopropyl-fluorophosphate, azinphosmethyl, chlorpyrifos, diazinon, dichlorvos, dimethoate, ethephon, malathion, methamidophos, naled, oxydemetonmethyl, parathion, fenthion, ethion, echothiophate, isofluorophate, trichlorfon, and/or tribufos.

Also provided herein are methods for treating patients exposed to nerve agents applying to a mucosal surface(s) of the nasal cavity or cavities of an individual (e.g., the mucosal surfaces of the anterior regions of the nose, the frontal sinus, the maxillary sinuses, and/or on each of the mucosal surfaces which overlie the turbinates covering the conchas) any of the pharmaceutical compositions or unit doses herein. In a related aspect, the method of treating a patient with nerve agent exposure in need of treatment from a nasal loading dose of an anticholinergic agent (e.g., atropine) and/or a cholinesterase reactivator agent (e.g., pralidoxime chloride). In another related aspect, the method of treating a patient with nerve agent exposure in need of treatment from a nasal loading dose of an anticholinergic agent (e.g., atropine), a cholinesterase reactivator agent (e.g., pralidoxime chloride), a vasoactive agent (e.g., epinephrine), and/or an anticonvulsive agent (e.g., diazepam). In yet another related aspect, the method of treating a patient with nerve agent exposure in need of treatment from a nasal loading dose of an anticholinergic agent (e.g., atropine), a cholinesterase reactivator agent (e.g., pralidoxime chloride, a vasoactive agent (e.g., epinephrine), an anticonvulsive agent (e.g., diazepam), a vasodilator (e.g., phentolamine), a COMT inhibitor (e.g., entacapone), at least one enabling agent, and/or at least one carrier and/or excipient.

The methods, kits, compositions, doses, or products herein are useful for treating patients. In some instances, the patient has minimal to severe respiratory distress including bronchorrhea and bronchospasms. In some instances, the patient has excess sweating and salivation, seizures, and paralysis. In some embodiments, the composition provides a fast onset time and is suitable for intranasal use.

In some embodiments, the intranasal dry powder composition is sufficient to improve respiratory function and breathing in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to reduce bronchorrhea and bronchospasms in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to decrease excess sweating and salivation, seizures, and paralysis in the patient within 60 minutes, 50 minutes, 40 minutes, 30 minutes, 20 minutes, 10 minutes, 5 minutes, 3 minutes, 2 minutes, or 1 minute after administration.

In some embodiments, the method of dilating a bronchus in a subject includes the intranasal administration of the dry powder composition disclosed herein. In some embodiments, the dilation occurs without substantial pulmonary inhalation. In some embodiments, the method of delivering epinephrine in a subject at least one of alpha-adrenergic receptors, beta-adrenergic receptors, or any combination thereof, include the intranasal administration of the dry powder composition disclosed herein. In some embodiments, the alpha-adrenergic receptors consist of the group including alpha-1 and alpha-2 adrenergic receptors. In some embodiments, the beta-adrenergic receptors consist of the group including beta-1, beta-2, and beta-3 adrenergic receptors. In some embodiments, delivery of epinephrine is localized. In some embodiments, delivery of epinephrine is systemic. In some embodiments, the method of treating a subject with asthma includes the intranasal administration of the dry powder composition disclosed herein. In some embodiments, the method of treating a subject with croup includes the intranasal administration of the dry powder composition disclosed herein. In some embodiments, the method of treating a subject by increasing the heart rate of the subject includes the intranasal administration of the dry powder composition disclosed herein. In some embodiments, the method of treating a subject by increasing the respiratory rate of the subject includes the intranasal administration of the dry powder composition disclosed herein. In some embodiments, the method of increasing the blood concentration of epinephrine in a subject includes the intranasal administration of the dry powder composition disclosed herein. In some embodiments, the method of treating pulmonary edema in a subject includes the intranasal administration of the dry powder composition disclosed herein. In some embodiments, the method of treating serum sickness in a subject in a subject includes the intranasal administration of the dry powder composition disclosed herein. In some embodiments, the method of counteracting bronchoconstriction effects in a subject following certain chemical exposures includes the intranasal administration of the dry powder composition disclosed herein.

The methods, kits, compositions, doses, or products herein are useful for treating patients. In some embodiments, the patient has bronchoconstriction, hypotension, and/or minimal or no cardiac activity. In some embodiments, the patient has low blood pressure. In some embodiments, the patient has hypotension. In some embodiments, the patient is experiencing hypotensive shock. In some embodiments, the composition also provides a fast onset time and is suitable for intranasal use.

In some embodiments, the intranasal dry powder composition is sufficient to increase arterial pressure in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to increase a mean arterial pressure in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to increase coronary perfusion pressure in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to resume a spontaneous circulation in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to relieve the bronchoconstriction in the patient within 60 minutes, 50 minutes, 40 minutes, 30 minutes, 20 minutes, 10 minutes, 5 minutes, 3 minutes, 2 minutes, or 1 minute after administration.

Also provided herein are methods for treating bronchospasm, cardiac arrest, hypotensive shock, or other situations requiring the need to implement cardiopulmonary resuscitation (CPR) and/or basic or advanced cardiac life support (ACLS) in an individual, including, applying to a mucosal surface(s) of the nasal cavity or cavities of an individual (e.g., the mucosal surfaces of the anterior regions of the nose, the frontal sinus, the maxillary sinuses, and/or on each of the mucosal surfaces which overlie the turbinates covering the conchas) any of the pharmaceutical compositions or unit doses herein by administering a vasoactive agent (e.g., epinephrine). In one embodiment, a nasal loading dose is an amount of epinephrine administered nasally that results in the systemic blood bioequivalent of intravenously (IV), intramuscularly (IM), or subcutaneously (SQ) administered epinephrine (e.g., 1 mg IV or 0.3 mg doses of EPIPEN®). In a related aspect, the method of treating a patient with cardiac arrest and/or bronchospasm in need of treatment with a composition including the nasal loading dose of about 0.05 mg to about 10 mg of a vasoactive agent (e.g., epinephrine), for example, about 0.5 mg to about 5 mg. In one embodiment, the composition includes about 0.75, 1.5, or 3.0 mg of the vasoactive agent (e.g., epinephrine) and optionally includes about 0.001 mg (or 1 µg) to 10 mg of a vasodilator (e.g., phentolamine), for example, about 0.1 mg to about 5 mg. In one embodiment, the composition includes about 0.1 to about 1 mg, or about 0.5 mg of the vasodilator (e.g., phentolamine). In one embodiment, the composition includes a pharmaceutically acceptable carrier mixture of about 1 to about 50 mg, for example about 10 to about 30 mg, about 15 to about 20 mg, or about 18 mg, and optionally, an agent that reduces mucosal transit time, an agent that increases mucosal absorption and/or adhesion, an agent that enhances mucosal transport, (or the enantiomers, diastereoisomers, racemates, and the salts of such compounds with pharmaceutically acceptable counterions), wherein the amounts are operable to be synergistic for the treatment of bronchospasm and/or cardiac arrest. When used in such low doses, compositions herein are operable to provide a sufficiently high peak blood plasma concentration of the vasoactive agent (e.g., epinephrine) of at least about: 2-fold, 3-5 fold, 5-7 fold, or 7-10 fold more than baseline levels rapidly after administration, within about: 60, 50, 40, 30, 20, 15, 10, 5, or 3 minutes to be effective in the treatment or reducing the symptoms of bronchospasm and/or cardiac arrest.

In some embodiments, the method herein further includes (a) initiating cardiopulmonary resuscitation (CPR), (b) using an automated external defibrillator (AED), or both (a) and (b). In some embodiments, the intranasal dry powder composition is administered if (a), (b), or both fail to increase the arterial pressure in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is administered if (a), (b), or both fail to increase the mean arterial pressure in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is administered if (a), (b), or both fail to increase coronary perfusion pressure in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is administered if (a), (b), or both fail to resume a spontaneous circulation in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is administered if (a), (b), or both fail to relieve the allergic reaction in the patient within 60 minutes, 50 minutes, 40 minutes, 30 minutes, 20 minutes, 10 minutes, 5 minutes, 3 minutes, 2 minutes, or 1 minute after administration.

The methods, kits, compositions doses or products herein are useful for treating patients. In some instances, the patient has risk for seizures, signs of seizure, or status epilepticus. In any cases, the compositions described herein are operable to provide a fast onset time and are suitable for intranasal use.

In some embodiments, the intranasal dry powder composition is sufficient to prevent, limit, or eliminate seizure activity in the patient within 60 minutes, 50 minutes, 40 minutes, 30 minutes, 20 minutes, 10 minutes, 5 minutes, 3 minutes, 2 minutes, or 1 minute after administration.

In another aspect, the methods, kits, compositions, doses, or products herein are useful for treating patients in a hospital. In some embodiments, the patient is not in a hospital. In some embodiments, the patient is in a hospital. In some embodiments, the patient is in a combat setting. In some embodiments, the patient is in a civil emergency setting. In some embodiments, the patient has a wound.

In yet another aspect, provided herein is a method of nasal delivery that employs a single use sterile premixed composition (dry powder or aqueous) containing an anticholinergic agent (e.g., atropine), a cholinesterase reactivator agent (e.g., pralidoxime chloride), a vasoactive agent (e.g., epinephrine), an anticonvulsive agent (e.g., diazepam), a vasodilator (e.g., phentolamine), a COMT inhibitor (e.g., entacapone), and/or other agents herein that are operable to be disposed of after use.

Location data is created in the present invention using one or more hardware and/or software components. By way of example and not limitation, location data is created using the Global Positioning System (GPS), low energy BLUETOOTH based systems such as beacons, wireless networks such as WIFI, Radio Frequency (RF) including RF Identification (RFID), Near Field Communication (NFC), magnetic positioning, and/or cellular triangulation. By way of example, location data is determined via an Internet Protocol (IP) address of a device connected to a wireless network. A wireless router is also operable to determine identities of devices connected to the wireless network through the router, and thus is operable to determine the locations of these devices through their presence in the connection range of the wireless router.

Figure 6:
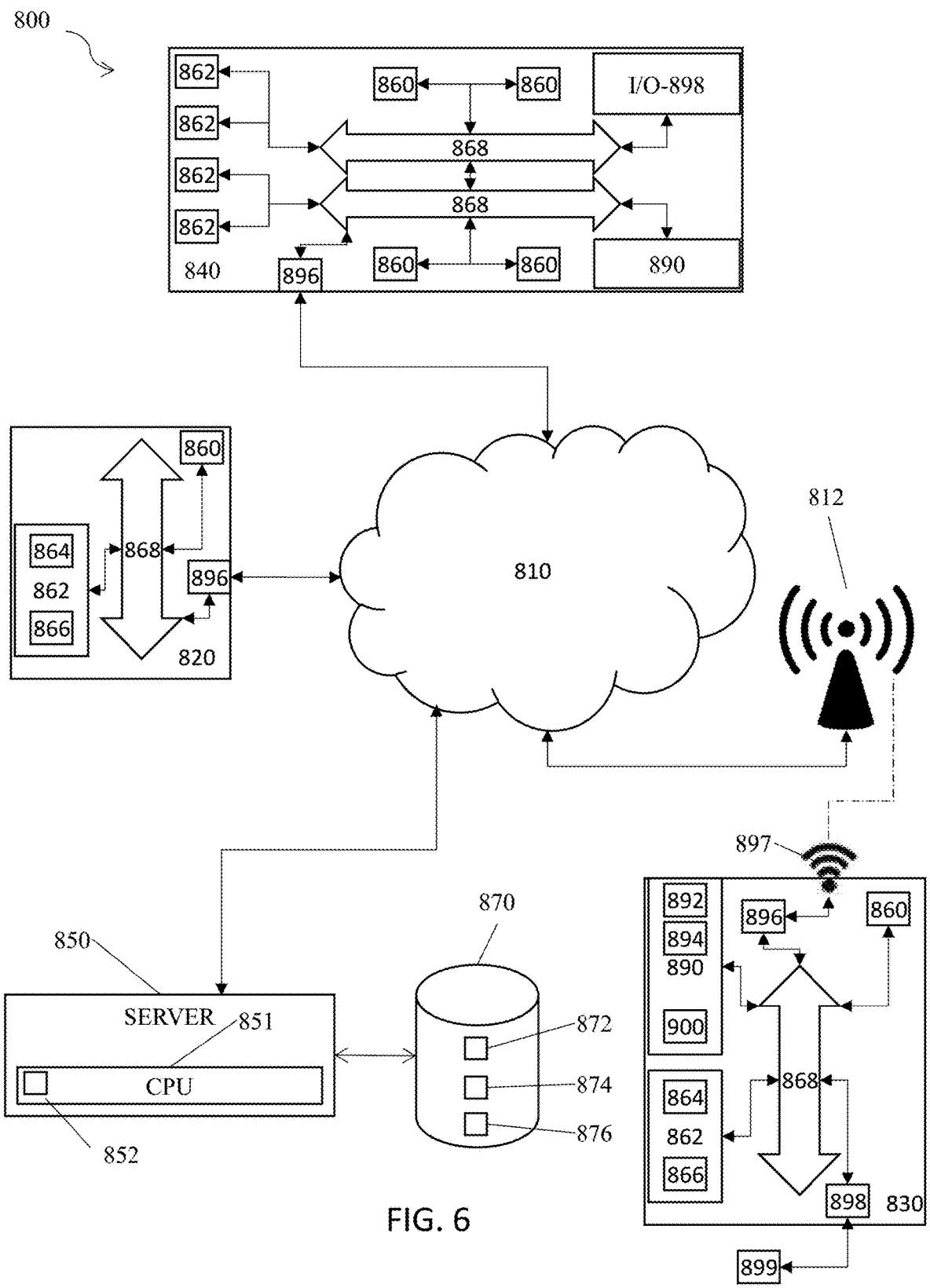
FIG. 6 is a schematic diagram of a system of the present invention.

FIG. 6 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 is operable to house an operating system 872, memory 874, and programs 876.

In one embodiment of the invention, the system 800 includes a network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 is operable to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of electronic devices including at least a processor and a memory, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in the present application.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is operable to additionally include components such as a storage device 890 for storing the operating system 892 and one or more application programs 894, a network interface unit 896, and/or an input/output controller 898. Each of the components is operable to be coupled to each other through at least one bus 868. The input/output controller 898 is operable to receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 is operable to be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 6, multiple processors 860 and/or multiple buses 868 are operable to be used, as appropriate, along with multiple memories 862 of multiple types (e.g., a combination of a DSP and a microprocessor, a plurality of microprocessors, one or more microprocessors in conjunction with a DSP core).

Also, multiple computing devices are operable to be connected, with each device providing portions of the necessary operations (e.g., a server bank, a group of blade servers, or a multi-processor system). Alternatively, some steps or methods are operable to be performed by circuitry that is specific to a given function.

According to various embodiments, the computer system 800 is operable to operate in a networked environment using logical connections to local and/or remote computing devices 820, 830, 840 through a network 810. A computing device 830 is operable to connect to a network 810 through a network interface unit 896 connected to a bus 868. Computing devices are operable to communicate communication media through wired networks, direct-wired connections or wirelessly, such as acoustic, RF, or infrared, through an antenna 897 in communication with the network antenna 812 and the network interface unit 896, which are operable to include digital signal processing circuitry when necessary. The network interface unit 896 is operable to provide for communications under various modes or protocols.

In one or more exemplary aspects, the instructions are operable to be implemented in hardware, software, firmware, or any combinations thereof. A computer readable medium is operable to provide volatile or non-volatile storage for one or more sets of instructions, such as operating systems, data structures, program modules, applications, or other data embodying any one or more of the methodologies or functions described herein. The computer readable medium is operable to include the memory 862, the processor 860, and/or the storage media 890 and is operable be a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further operable to be transmitted or received over the network 810 via the network interface unit 896 as communication media, which is operable to include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

In one embodiment, the computer system 800 is within a cloud-based network. In one embodiment, the server 850 is a designated physical server for distributed computing devices 820, 830, and 840. In one embodiment, the server 850 is a cloud-based server platform. In one embodiment, the cloud-based server platform hosts serverless functions for distributed computing devices 820, 830, and 840.

In another embodiment, the computer system 800 is within an edge computing network. The server 850 is an edge server, and the database 870 is an edge database. The edge server 850 and the edge database 870 are part of an edge computing platform. In one embodiment, the edge server 850 and the edge database 870 are designated to distributed computing devices 820, 830, and 840. In one embodiment, the edge server 850 and the edge database 870 are not designated for distributed computing devices 820, 830, and 840. The distributed computing devices 820, 830, and 840 connect to an edge server in the edge computing network based on proximity, availability, latency, bandwidth, and/or other factors.

It is also contemplated that the computer system 800 is operable to not include all of the components shown in FIG. 6, is operable to include other components that are not explicitly shown in FIG. 6, or is operable to utilize an architecture completely different than that shown in FIG. 6. The various illustrative logical blocks, modules, elements, circuits, and algorithms described in connection with the embodiments disclosed herein are operable to be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

The above-mentioned examples are provided to serve the purpose of clarifying the aspects of the invention, and it will be apparent to one skilled in the art that they do not serve to limit the scope of the invention. By nature, this invention is highly adjustable, customizable and adaptable. The above-mentioned examples are just some of the many configurations that the mentioned components can take on. All modifications and improvements have been deleted herein for the sake of conciseness and readability but are properly within the scope of the present invention.

The invention claimed is:

1. A device for intranasal administration of a pharmaceutical composition comprising:
   a reservoir and a means for discharging one or more doses of the pharmaceutical composition, wherein the reservoir contains a quantity of the pharmaceutical composition; and
   wherein the pharmaceutical composition comprises:
      an anti-muscarinic agent, wherein the anti-muscarinic agent is atropine or a pharmaceutically acceptable salt thereof, wherein the pharmaceutical composition provides a dose of about 0.1 mg to about 10 mg of the atropine or the pharmaceutically acceptable salt thereof;
      a cholinesterase reactivator, wherein the cholinesterase reactivator is 2-pyridine aldoxime methyl chloride, wherein the pharmaceutical composition provides a dose of about 1 mg to about 1000 mg of the 2-pyridine aldoxime methyl chloride;
      a vasoactive agent, wherein the vasoactive agent is epinephrine or a pharmaceutically acceptable salt thereof, wherein the pharmaceutical composition provides a dose of about 0.01 mg to about 10 mg of the epinephrine or the pharmaceutically acceptable salt thereof; and
      an anti-convulsant agent, wherein the anti-convulsant agent is diazepam or a pharmaceutically acceptable salt thereof, wherein the pharmaceutical composition provides a dose of about 0.1 mg to about 20 mg of the diazepam or the pharmaceutically acceptable salt thereof.

2. The device of claim 1, wherein the device includes a nasal probe, and wherein the nasal probe is operable to be replaced between discharges.

3. The device of claim 1, wherein the pharmaceutical composition further comprises a vasodilator, wherein the vasodilator is phentolamine or a pharmaceutically acceptable salt thereof, wherein the pharmaceutical composition provides a dose of about 0.01 mg to about 10 mg of the phentolamine or the pharmaceutically acceptable salt thereof.

4. The device of claim 1, wherein the pharmaceutical composition further comprises a catechol-o-methyl transferase (COMT) inhibitor.

5. The device of claim 4, wherein the COMT inhibitor is entacapone or a pharmaceutically acceptable salt thereof, wherein the pharmaceutical composition provides a dose of about 5 mg to about 200 mg of the entacapone or the pharmaceutically acceptable salt thereof.

6. The device of claim 1, wherein the pharmaceutical composition further comprises an anticaking agent.

7. The device of claim 6, wherein the anticaking agent is tribasic calcium phosphate.

8. The device of claim 1, wherein the atropine or the pharmaceutically acceptable salt thereof, the 2-pyridine aldoxime methyl chloride, the epinephrine or the pharmaceutically acceptable salt thereof, and/or the diazepam or the pharmaceutically acceptable salt thereof are particles having a median particle diameter of about 30 μM.

9. The device of claim 1, wherein the pharmaceutical composition further comprises at least one antihistamine.

10. The device of claim 1, wherein the pharmaceutical composition further comprises at least one steroid.

11. The device of claim 1, wherein the pharmaceutical composition further comprises a carrier.

12. The device of claim 11, wherein the carrier comprises at least one cellulose and/or at least one starch.

13. The device of claim 1, wherein the pharmaceutical composition further comprises one or more agents selected from a group consisting of an excipient, a preservative, a humectant, a thickening agent, a solubilizing agent, a taste-masking agent, a scent-masking agent, an antioxidant enzyme, a viscosity enhancing agent, a dispersing agent, a surfactant, a chelator, an antihistamine, a colorant, or any combination thereof.

14. The device of claim 1, wherein the pharmaceutical composition further comprises one or more agents selected from a group consisting of a mucosal permeation or penetration enhancer, a mucoadhesive, a mucosal transit slowing agent, a mucosal transport enhancer, or any combination thereof.

15. A kit for intranasal administration of a pharmaceutical composition comprising:
   at least one device, wherein each of the at least one device includes a reservoir and a means for discharging one or more doses of the pharmaceutical composition, wherein the reservoir contains a quantity of the pharmaceutical composition; and
   wherein the pharmaceutical composition comprises:
      an anti-muscarinic agent, wherein the anti-muscarinic agent is atropine or a pharmaceutically acceptable salt thereof, wherein the pharmaceutical composition provides a dose of about 0.1 mg to about 10 mg of the atropine or the pharmaceutically acceptable salt thereof;
      a cholinesterase reactivator, wherein the cholinesterase reactivator is 2-pyridine aldoxime methyl chloride, wherein the pharmaceutical composition provides a dose of about 1 mg to about 1000 mg of the 2-pyridine aldoxime methyl chloride;
      a vasoactive agent, wherein the vasoactive agent is epinephrine or a pharmaceutically acceptable salt thereof, wherein the pharmaceutical composition provides a dose of about 0.01 mg to about 10 mg of the epinephrine or the pharmaceutically acceptable salt thereof; and
      an anti-convulsant agent, wherein the anti-convulsant agent is diazepam or a pharmaceutically acceptable salt thereof, wherein the pharmaceutical composition provides a dose of about 0.1 mg to about 20 mg of the diazepam or the pharmaceutically acceptable salt thereof.

16. The kit of claim 15, wherein the at least one device is enclosed in a pouch or a hard case.

17. The kit of claim 16, wherein the pouch or the hard case is water resistant or waterproof.

18. The kit of claim 16, wherein the pouch or the hard case includes an exterior finish comprising a camouflage.

19. The kit of claim 16, wherein the pouch and/or the hard case is MOLLE-compatible.

20. A device for intranasal administration of a pharmaceutical composition comprising:
   a reservoir and a means for discharging one or more doses of the pharmaceutical composition, wherein the reservoir contains a quantity of the pharmaceutical composition; and wherein the pharmaceutical composition comprises:
- an anti-muscarinic agent, wherein the anti-muscarinic agent is atropine or a pharmaceutically acceptable salt thereof, wherein the pharmaceutical composition provides a dose of about 0.1 mg to about 10 mg of the atropine or the pharmaceutically acceptable salt thereof;
- a cholinesterase reactivator, wherein the cholinesterase reactivator is 2-pyridine aldoxime methyl chloride, wherein the pharmaceutical composition provides a dose of about 1 mg to about 1000 mg of the 2-pyridine aldoxime methyl chloride;
- a vasoactive agent, wherein the vasoactive agent is epinephrine or a pharmaceutically acceptable salt thereof, wherein the pharmaceutical composition provides a dose of about 0.01 mg to about 10 mg of the epinephrine or the pharmaceutically acceptable salt thereof;
- an anti-convulsant agent, wherein the anti-convulsant agent is diazepam or a pharmaceutically acceptable salt thereof, wherein the pharmaceutical composition provides a dose of about 0.1 mg to about 20 mg of the diazepam or the pharmaceutically acceptable salt thereof;
- a vasodilator, wherein the vasodilator is phentolamine or a pharmaceutically acceptable salt thereof, wherein the pharmaceutical composition provides a dose of about 0.01 mg to about 10 mg of the phentolamine or the pharmaceutically acceptable salt thereof; and
- a carrier.

* * * * *